(12) United States Patent
O'Toole et al.

(10) Patent No.: US 12,220,434 B2
(45) Date of Patent: *Feb. 11, 2025

(54) ALTERING THE INTESTINAL MICROBIOME IN CYSTIC FIBROSIS

(71) Applicants: Trustees of Dartmouth College, Hanover, NH (US); Dartmouth-Hitchcock Clinic, Lebanon, NH (US)

(72) Inventors: George A. O'Toole, Hanover, NH (US); Juliette C. Madan, Lyme, NH (US)

(73) Assignees: Trustees of Dartmouth College, Hanover, NH (US); Dartmouth-Hitchcock Clinic, Lebanon, NH (US)

(*) Notice: Subject to any disclaimer, the term of this patent is extended or adjusted under 35 U.S.C. 154(b) by 13 days.

This patent is subject to a terminal disclaimer.

(21) Appl. No.: 17/664,156

(22) Filed: May 19, 2022

(65) Prior Publication Data

US 2022/0362310 A1 Nov. 17, 2022

Related U.S. Application Data

(63) Continuation of application No. 16/979,824, filed as application No. PCT/US2019/024045 on Mar. 26, 2019, now Pat. No. 11,351,208.

(60) Provisional application No. 62/649,230, filed on Mar. 28, 2018.

(51) Int. Cl.
| | | |
|---|---|---|
| A61K 35/745 | (2015.01) | |
| A61K 35/741 | (2015.01) | |
| A61K 35/744 | (2015.01) | |
| A61K 45/06 | (2006.01) | |
| A61P 1/00 | (2006.01) | |
| A61P 11/00 | (2006.01) | |

(52) U.S. Cl.
CPC .......... *A61K 35/745* (2013.01); *A61K 35/741* (2013.01); *A61K 35/744* (2013.01); *A61K 45/06* (2013.01); *A61P 1/00* (2018.01); *A61P 11/00* (2018.01)

(58) Field of Classification Search
None
See application file for complete search history.

(56) References Cited

U.S. PATENT DOCUMENTS

2014/0221424 A1 8/2014 Zha
2016/0199424 A1 7/2016 Berry et al.

FOREIGN PATENT DOCUMENTS

WO WO 2019/191073 A1 10/2019

OTHER PUBLICATIONS

Hoen et al., *J. Pediatr.*, 167(1): 138-47 (2015).
Madan et al., mBio, 3(4):e00251-12 (2012).
The United States Patent and Trademark Office, International Search Report in International Application No. PCT/US19/24045.
The United States Patent and Trademark Office, Written Opinion in International Application No. PCT/US19/24045.

*Primary Examiner* — Brian Gangle
(74) *Attorney, Agent, or Firm* — Neal, Gerber & Eisenberg LLP

(57) ABSTRACT

The present disclosure relates to a method of altering intestinal microbiome in a patient having cystic fibrosis comprising administering at least one of *Bifidobacterium* and/or *Bacteroides* to a patient and allowing the *Bifidobacterium* and/or *Bacteroides* to alter the intestinal microbiome.

31 Claims, 25 Drawing Sheets

ALTERING THE INTESTINAL MICROBIOME IN CYSTIC FIBROSIS

CROSS REFERENCE TO RELATED APPLICATIONS

This patent application is a continuation of U.S. patent application Ser. No. 16/979,824, filed on Sep. 10, 2020 as a National Stage Entry of International Patent Application No. PCT/US2019/024045, filed on Mar. 26, 2019, which claims priority to U.S. Provisional Patent Application No. 62/649,230, filed on Mar. 28, 2018. The entire contents of each of the aforementioned applications are fully incorporated herein by reference.

FEDERALLY SPONSORED RESEARCH OR DEVELOPMENT

This invention was made with government support under AI083256, HL134598, GM104416, GM103413, OD023275, ES022832, ES007373, ES018175 awarded by the National Institutes of Health and RD83459901 awarded by the Environmental Protection Agency. The government has certain rights in the invention.

TECHNICAL FIELD

Compositions and methods for treating cystic fibrosis and for diagnosing, predicting, or preventing cystic fibrosis-associated clinical outcomes in subjects based on intestinal bacterial compositions or microbiomes.

BACKGROUND

Cystic fibrosis (CF) is an autosomal recessive disease, known to significantly alter the microenvironments in the airways, intestines and other organs, and is associated with systemic complications such as growth failure, chronic infections, pancreatic insufficiency, and ultimately premature mortality. While a great deal of attention has been focused on therapies to treat the chronic airway infections that are often the proximal cause of mortality for these patients, it is the gastrointestinal complications that are at the forefront for patients with CF in early life. Young patients with CF experience difficulty in absorbing nutrients secondary to meconium ileus and pancreatic insufficiency. Poor weight gain is common, resulting in the need for a high calorie diet starting early in life and treatment with pancreatic enzyme replacement therapy. Additionally, alterations in the intestinal microbiome in infancy or early life (the first 12 months of life) have been associated with alterations in competent immune training with resultant increased risk of lifelong disease in healthy populations.

Previously, it has been shown that select genera (e.g., *Enterococcus, Escherichia*) colonizing the airway of patients with CF tend to first appear in the intestines. Furthermore, breastfed infants showed a longer time until their first pulmonary exacerbation, with 20% of breastfed children having no exacerbation over the first 30 months of life, compared to exclusively formula-fed infants, all of whom suffered exacerbations by 9 months. Further, previous studies have shown that higher levels of diverse *Streptococcus* species in the lungs of adult patients with CF are associated with clinical stability. Additionally, commensal *Streptococcus* species have been shown to reduce host inflammation response by down regulating pro-inflammatory IL-8 production or activating the release of anti-inflammatory IL-10 by healthy host cells. Further, some *B. fragilis* strains produce enterotoxins that can stimulate the production of IL-8. Specifically, exposing the apical face of intestinal epithelial cells to such a toxin resulted in the increased production of IL-8 from the basolateral face of the same cell monolayer. These data suggest that changes to the microbiota in the lumen of the gut can have systemic effects on immune responses, inflammation, and disease outcomes.

However, the mechanism(s) by which intestinal microbial communities impact lung function and pulmonary exacerbation is not still clear. Furthermore, while enzyme replacement therapy has clearly had positive, transformative impacts on patients with CF, these patients still have underlying defects in intestinal microbiota, and suggest room for improvement in such therapeutic interventions. Thus, a new method for treating cystic fibrosis and diagnosing clinical risk of poor outcomes associated with cystic fibrosis is now warranted.

SUMMARY

The present disclosure provides, in part, bacterial compositions and methods of use thereof. The bacterial compositions may be used, without limitation, to alter the intestinal microbiota, e.g., to modify, improve, or provide a beneficial microbiota, or to treat or diagnose *Pseudomonas aeruginosa* (*P. aeruginosa*) infection or chronic colonization, pulmonary exacerbation, or other clinical outcomes associated with cystic fibrosis in a subject in need thereof. In some aspects, the bacterial compositions and methods rely on microbes associated with immune programming such as *Bacteroides* and *Bifidobacterium* to alter the intestinal microbiome, in a specific window of development or age, and subsequently impact systemic health.

As disclosed herein, while compared to healthy controls, patients (infants) with CF show reduced *Bacteroides* and *Bifidobacterium* in their intestinal microbiome, even after adjusting for antibiotic treatment. Further, when infants with CF were divided into groups with and without pulmonary exacerbation, there was a significant association between higher levels of *Streptococcus* and *Ruminococcus* in the intestinal microbiome and a reduced likelihood of pulmonary exacerbation. Also identified are several metabolic pathways enriched or under represented among the microbial communities in patients with CF. These findings further establish a link between gastrointestinal microbiota and airway disease, and provide the opportunity for probiotic therapeutic interventions.

In one embodiment, a method of altering the intestinal microbiome in a patient diagnosed with cystic fibrosis comprises administering at least one of *Bifidobacterium* and/or *Bacteroides* to a patient and allowing the *Bifidobacterium* and/or *Bacteroides* to alter the intestinal microbiome.

In another embodiment, a method for altering the intestinal microbiome in a subject having cystic fibrosis comprises administering at least one of *Streptococcus* and/or *Ruminococcus* to the subject and allowing the *Streptococcus* and/or *Ruminococcus* to alter the intestinal microbiome.

In another embodiment, a method of treating a patient with cystic fibrosis comprises:
 a. determining from a fecal sample whether the subject has a decreased level of *Bifidobacterium, Bacteroides, Faecalibacterium, Clostridiales, Roseburia, Ruminococcaceae, Eubacterium, Streptococcus*, and/or *Ruminococcus* relative to a healthy control population and
 b. if it is determined that the patient has a decreased level of *Bifidobacterium, Bacteroides, Faecalibacterium,*

*Clostridiales, Roseburia, Ruminococcaceae, Eubacterium, Streptococcus*, and/or *Ruminococcus* relative to a healthy control population administering an effective amount of cystic fibrosis therapy to the subject thereby treating cystic fibrosis, wherein the cystic fibrosis therapy comprises one or more of:
  i. at least one pancreatic enzyme replacement product;
  ii. at least one probiotic;
  iii. at least one prebiotic;
  iv. at least one antibiotic;
  v. at least one anti-inflammatory medication;
  vi. at least one mucus-thinning drug;
  vii. at least one cystic fibrosis transmembrane conductance regulator (CFTR) function-improving medication;
  viii. at least one bronchodilator or inhaled medication.

In another embodiment, a method of diagnosing the risk of *P. aeruginosa* infection or chronic colonization, or pulmonary exacerbation, in a patient having cystic fibrosis comprises:
  a. determining from a biological sample from the patient whether the patient has a decreased level of *Bifidobacterium* and/or *Bacteroides* by comparing the level of *Bifidobacterium* and/or *Bacteroides* in the patient with the level of *Bifidobacterium* and/or *Bacteroides* in a healthy control population;
  b. diagnosing the patient as having an increased risk of *P. aeruginosa* infection or chronic colonization, or pulmonary exacerbation, if the patient has a decreased level of *Bifidobacterium* and/or *Bacteroides* compared to the healthy control population.

In another embodiment, a method of reducing a pro-inflammatory response and/or promoting an anti-inflammatory response in a patient having cystic fibrosis, the method comprises administering at least one of *Bifidobacterium* and/or *Bacteroides* to the patient, wherein prior to said administration a sample from the patient has been tested to determine a level of *Bifidobacterium* and/or *Bacteroides*.

In another embodiment, a method of preventing, delaying the onset, reducing the severity, and/or reducing the duration of an infection by a pathogen, or an exacerbation thereof, in a patient in need thereof comprises administering to the patient at least one of *Bifidobacterium* and/or *Bacteroides* to the patient, wherein prior to said administration a sample from the patient has been tested to determine a level of *Bifidobacterium* and/or *Bacteroides*.

The present disclosure demonstrates that infants with CF ≤1 year of age, the youngest such group analyzed to date, show a distinct stool microbiota compared with control infants of a comparable age. Associations between gut microbiome and airway exacerbation events were detected in the cohort of infants with CF. The in vitro studies presented herein provided a possible mechanism. In addition, the data presented herein clarified that current therapeutics do not establish a healthy-like gastrointestinal microbiota in infants with CF. Interventions that direct the gastrointestinal microbiota closer to a healthy state may provide systemic benefits to these patients during a critical window of immune programming that might have implications for lifelong health.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

In FIG. 3A, samples from patients with CF at 4 months cluster separately from samples from healthy controls (PERMANOVA p=0.002). In FIG. 3B, samples from patients with CF at 1 year continue to cluster separately from samples from healthy controls (PERMANOVA p=0.001). In FIG. 3C, samples from healthy controls at 4 months cluster separately from samples from 12 months old healthy controls (PERMANOVA p=0.001). In contrast, FIG. 3D show that samples from patients with CF at 4 months and 12 months do not cluster separately from each other (PERMANOVA p=0.396). FIG. 3E shows PCoA plots generated from samples of all four different groups as presented in FIGS. 3A-3D.

FIG. 4A shows the relative abundance at 4 months in 14 samples from patients with CF and 20 samples from healthy controls. FIG. 4B shows the relative abundance at 12 months in 13 samples from patients with CF and 45 samples from healthy controls.

FIG. 5A shows that patients with CF showed a significantly lower relative abundance of *Bifidobacterium* than healthy controls at 12 months of age when the data are analyzed as a whole (p=0.04). FIG. 5B shows that patients with CF showed a significantly lower relative abundance of *Bacteroides* than healthy controls after adjusting for antibiotics (p=0.03, Wilcoxon rank sum test with Bonferroni correction).

DETAILED DESCRIPTION

Figure 1:
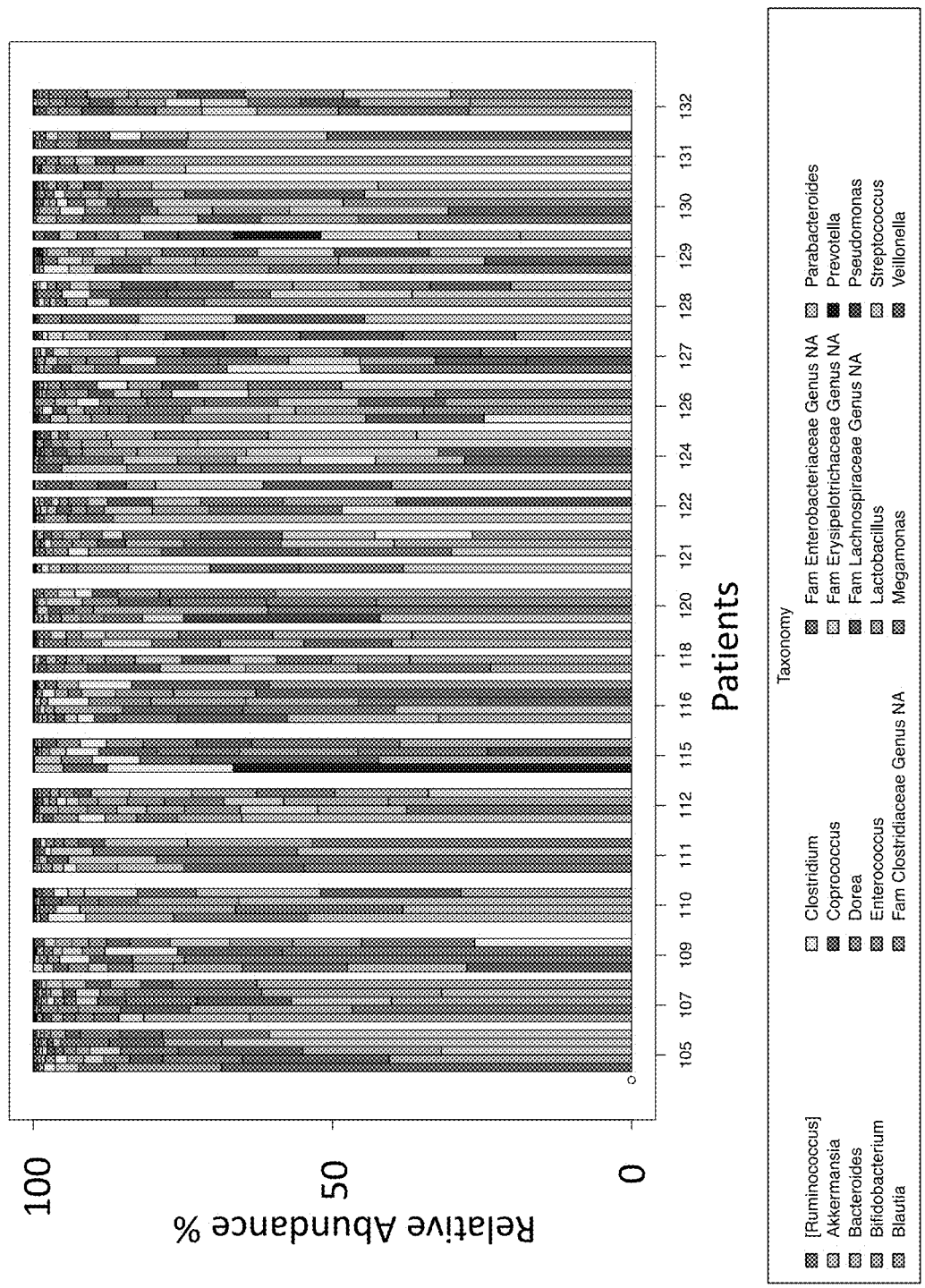
FIG. 1 provides the relative abundance of the intestinal microbiome in patients with CF over their first year of life. The y axis for stacked bar plots represents the relative abundance (0-100%) of top twenty operational taxonomic units (OTU) (assigned at the genus level, when possible, or otherwise at the next lowest taxonomic level), each OTU being represented by a distinct color as indicated in the taxonomy legend. The x axis represents patient number (105-132) and serial samples at progressive months up to 1 year.

The present disclosure provides, in part, bacterial compositions and methods of use thereof. The bacterial compositions may be used, without limitation, to alter the intestinal microbiota (including modify, improve, or provide a beneficial microbiota), or to treat cystic fibrosis, or to diagnose, predict, or prevent the risk of *P. aeruginosa* infection or chronic colonization, pulmonary exacerbation, gastrointestinal tract-related outcomes, or other clinical outcomes associated with cystic fibrosis, in a subject in need thereof.

A. Bacterial Compositions

In some embodiments, bacterial compositions, as described herein, include one or more bacteria of the genera *Bacteroides* or one or more bacteria of the genera *Bifidobacterium* or one or more bacteria of the genera *Faecalibacterium*, or one or more bacteria of the family Clostridiales or one or more bacteria of the genera *Roseburia* or one or more bacteria of the family Ruminococcaceae or one or more bacteria of the genera *Eubacterium* or one or more bacteria of the genera *Streptococcus* or one or more bacteria of the genera *Ruminococcus*.

In some embodiments, bacterial compositions as described herein include two or more bacteria of the genera/family *Bacteroides, Bifidobacterium, Faecalibacterium, Clostridiales, Roseburia, Ruminococcaceae, Eubacterium, Streptococcus* and *Ruminococcus*.

In some embodiments, bacterial compositions as described herein include three or more bacteria of the genera/family *Bacteroides, Bifidobacterium, Faecalibacterium, Clostridiales, Roseburia, Ruminococcaceae, Eubacterium, Streptococcus* and *Ruminococcus*.

In some embodiments, bacterial compositions as described herein include four or more bacteria of the genera/family *Bacteroides, Bifidobacterium, Faecalibacterium, Clostridiales, Roseburia, Ruminococcaceae, Eubacterium, Streptococcus* and *Ruminococcus*.

In some embodiments, bacterial compositions as described herein include five or more bacteria of the genera/family *Bacteroides, Bifidobacterium, Faecalibacterium, Clostridiales, Roseburia, Ruminococcaceae, Eubacterium, Streptococcus* and *Ruminococcus*.

In some embodiments, bacterial compositions as described herein include six or more, seven or more, eight or more, or all nine of the genera/family *Bacteroides, Bifidobacterium, Faecalibacterium, Clostridiales, Roseburia, Ruminococcaceae, Eubacterium, Streptococcus* and *Ruminococcus*.

In any of the embodiments described herein, the bacterial composition can comprise any combination of two, three, four, five six, seven, eight or nine bacteria of the genera/family *Bacteroides, Bifidobacterium, Faecalibacterium, Clostridiales, Roseburia,* Ruminococcaceae, *Eubacteriums, Streptococcus* and *Ruminococcus*.

In some embodiments, bacterial compositions as described herein include both *Bacteroides* and *Bifidobacterium*. In some embodiments, bacteria of the genera *Bifidobacterium* include *Bifidobacterium* theta.

In some embodiments, bacterial compositions as described herein include one or more bacteria of the genera *Streptococcus* or one or more bacteria of the family *Ruminococcus*.

In some embodiments, bacterial compositions as described herein include one or more bacteria of the genera *Streptococcus*.

In some embodiments, bacteria of the genera *Streptococcus* include one or more of *S. bovis, S. gallolyticus, S. macedonicus, S. alactolyticus, S. vestibularis, S. salivarius, S. mitis, S. parasanguinis, S. lutetiensis, S. equinus, S. infantarius*, or operational taxonomic unit (OTU) encompassing said species.

In some embodiments, bacterial compositions as described in the preceding paragraphs of this section do not comprise bacteria of the family Clostridiales.

In some embodiments, a bacterial composition as described herein include bacteria as described herein, present in treated fecal material from a healthy donor or individual that does not have CF or a patient diagnosed with or treated for cystic fibrosis. Such bacterial compositions may be "directly isolated" and not resulting from any culturing or other process that results in or is intended to result in replication of the population after obtaining the fecal material. In some embodiments, bacteria as described herein include bacterial spores. In some embodiments, the bacterial compositions may be obtained from single bacterium or mixed bacteria having been grown in culture.

In some embodiments, a bacterial composition as described herein includes human bacterial strains. In alternative embodiments, a bacterial composition as described herein includes bacterial strains not generally found in humans.

In some embodiments, a bacterial composition as described herein includes bacteria capable of colonizing the gastrointestinal tract of a subject receiving the bacterial composition.

In some embodiments, a bacterial composition as described herein includes live bacteria.

In some embodiments, a bacterial composition as described herein includes substantially pure bacteria of the genera/family *Bacteroides, Bifidobacterium, Faecalibacterium, Clostridiales, Roseburia, Ruminococcaceae, Eubacterium, Streptococcus* and/or *Ruminococcus*. By "substantially pure" or "isolated" is meant bacteria of the genera/family *Bacteroides, Bifidobacterium, Faecalibacterium, Clostridiales, Roseburia, Ruminococcaceae, Eubacterium, Streptococcus* and/or *Ruminococcus* that are separated from the components that naturally accompany it, in for example, fecal matter or in the gastrointestinal tract. Typically, a bacterial composition as described herein is substantially pure when it is at least 50%, 60%, 70%, 75%, 80%, or 85%, or over 90%, 95%, or 99% by weight, of the total material in a sample. A substantially pure bacterial composition, as described herein, can be obtained, for example, by extraction from a natural source, such as fecal material, gastrointestinal tract, or other bodily fluid or material, or from bacterial cultures, for example, cultures of any of the bacteria described herein, such as *Bacteroides, Bifidobacterium, Faecalibacterium, Clostridiales, Roseburia, Ruminococcaceae, Eubacterium, Streptococcus* and/or *Ruminococcus*. By "substantially pure" or "isolated" the application can be referring to the component bacteria that make up the culture (adding, for example, *Bacteroides* that is 95% pure) or it can refer to the entire bacterial composition (the bacterial composition is 95% pure, meaning 95% comes from the component bacteria when added together, such as 50% *Bacteroides*, 30% *Bifidobacterium*, and 15% *Faecalibacterium*, and only 5% of components that natural accompany the bacteria such as fecal matter).

In some embodiments, a substantially pure bacterial composition, as described herein, is obtained, for example, by extraction from a natural source, such as fecal material, gastrointestinal tract, or other bodily fluid or material, from a healthy individual, an individual who does not have CF, or an individual who is being treated for or has been diagnosed with CF.

B. Microbiome Treatment

Bacterial compositions, as described herein, are used to alter the intestinal microbiota or to treat or protect against disease progression in cystic fibrosis, in particular, pulmonary exacerbation, or *P. aeruginosa* or other pathogenic microbial infection, in a subject in need thereof. Such other pathogenic microbial infections include, without limitation, infections with *Staphylococcus aureus, Pseudomonas aeruginosa, Stenotrophomonas, Haemophilus influenzae*, nontuberculous mycobacterium (including but not limited to *Mycobacteria abcessus* or *Mycobacteria avium*), *Burkholderia cepacia* complex, viral or fungal infection, or co-infections with multiple pathogens. In some embodiments, treating or protecting against disease progression in cystic fibrosis results in the prevention of pulmonary exacerbation or *P. aeruginosa* or other pathogenic microbial infection in the subject. In some embodiments, a bacterial composition, as described herein, is used to alter intestinal microbiota or to treat or protect against other pathogenic microbial infection associated with pulmonary exacerbation, in a subject in need thereof.

In some embodiments, a bacterial composition, as described herein, may be a therapeutic (including prophylactic) composition.

In some embodiments, a bacterial composition may be a therapeutic (including prophylactic) composition including one or more bacteria of the genera/family *Bacteroides, Bifidobacterium, Faecalibacterium, Clostridiales, Roseburia, Ruminococcaceae, Eubacterium, Streptococcus* and/or *Ruminococcus*.

An "effective amount" of a bacterial composition, as used herein, includes an amount sufficient to colonize the gastrointestinal tract of a subject for a suitable period of time as determined, for example, by detecting the presence of one or more bacteria of the genera/family *Bacteroides, Bifidobacterium, Faecalibacterium, Clostridiales, Roseburia, Ruminococcaceae, Eubacterium, Streptococcus* and/or *Ruminococcus*, or their metabolic byproducts associated with clinical outcomes (including, without limitation, butyrate), in a sample, such as a fecal sample, from the subject at specific periods after administration.

In some embodiments, an effective amount includes a therapeutically effective amount.

A "therapeutically effective amount" refers to an amount effective, at dosages and for periods of time necessary, to achieve the desired therapeutic result, such as treatment, prevention, or amelioration of cystic fibrosis, pulmonary exacerbation, or *P. aeruginosa* or other pathogenic microbial infection. A therapeutically effective amount of a bacterial composition may vary according to factors such as the disease state, age, sex, and weight of the subject, and the ability of the bacterial composition to elicit a desired response in the individual. Dosage regimens may be adjusted to provide the optimum therapeutic response. A therapeutically effective amount is also one in which any toxic or detrimental effects of the bacterial composition are outweighed by the therapeutically beneficial effects. Ultimately, the prescribers or researchers will decide the appropriate amount and dosage regimen. Such determinations are routine to one of ordinary skill in the art.

Conventional pharmaceutical or nutraceutical practice may be employed to provide suitable formulations or compositions to administer a bacterial composition, as described herein, to subjects suffering from or presymptomatic for cystic fibrosis, pulmonary exacerbation, *P. aeruginosa* infection, or any other CF-associated clinical outcomes. Any appropriate route of administration may be employed, for example, dermal, intranasal, inhalation aerosol, topical, gavage, rectal or oral administration.

The bacterial compositions can be in a variety of forms. These forms include, e.g., lyophilized, liquid, semi-solid and solid dosage forms, such as liquid solutions, dispersions or suspensions, tablets, pills, powders, liposomes, and suppositories. The preferred form depends, in part, on the intended mode of administration and application. Administration includes oral administration, nasogastric administration, rectal administration, and other forms of administration to the gastrointestinal tract.

Bacterial compositions, as described herein, can be formulated as a nutraceutical composition, such as medical foods, nutritional or dietary supplements, food products or beverage products, and include a nutraceutically acceptable carrier. As used herein, a "nutraceutically acceptable carrier" refers to, and includes, any and all solvents, dispersion media, coatings, antibacterial and antifungal agents, isotonic and absorption delaying agents, and the like that are physiologically compatible. The compositions can include a nutraceutically acceptable salt, e.g., an acid addition salt or a base addition salt. In some embodiments, the nutraceutically acceptable carrier is suitable for pediatric use.

Bacterial compositions, as described herein, can be formulated as a pharmaceutical composition and include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. In some embodiments, the pharmaceutically acceptable carrier is suitable for pediatric use.

II. DIAGNOSTIC METHODS

In some embodiments, a method diagnosing the risk of cystic fibrosis-associated clinical outcomes in a patient having cystic fibrosis comprises (1) determining whether the subject has a decreased level of *Bacteroides, Bifidobacterium, Faecalibacterium, Clostridiales, Roseburia*, Ruminococcaceae, and/or *Eubacterium*, relative to a healthy control population and (2) diagnosing the patient as having an increased risk of *P. aeruginosa* infection if the patient has a decreased level of *Bacteroides, Bifidobacterium, Faecalibacterium, Clostridiales, Roseburia*, Ruminococcaceae, and/or *Eubacterium*, relative to a healthy control population.

In some embodiments, a method diagnosing the risk of *P. aeruginosa* infection in a patient having cystic fibrosis comprises determining whether the subject has a decreased level of *Bacteroides, Bifidobacterium, Faecalibacterium, Clostridiales, Roseburia*, Ruminococcaceae, and/or *Eubacterium*, relative to a healthy control population; diagnosing the patient as having an increased risk of *P. aeruginosa* infection if the patient has a decreased level of *Bacteroides, Bifidobacterium, Faecalibacterium, Clostridiales, Roseburia*, Ruminococcaceae, and/or *Eubacterium*, relative to a healthy control population. In some embodiments, the method diagnoses the likelihood of *P. aeruginosa* infection. In some embodiments, the method aids in the determination of the time to onset of *P. aeruginosa* infection.

In some embodiments, the method comprises obtaining a fecal sample from a patient. In some embodiments, the fecal sample is obtained from a patient age 2 or less, age 18 months or less, age 12 months or less, age 6 months or less, or age 4 months of less. In some embodiments, the 16S rRNA sequencing or whole genome/metagenomics sequencing is used to determine the relative abundance of intestinal microbes in the fecal sample.

In some embodiments, a method diagnosing the risk of *P. aeruginosa* infection in a patient having cystic fibrosis comprises determining whether the subject has a decreased level of *Bacteroides* and/or *Bifidobacterium*, relative to a healthy control population; if the patient has a decreased level of *Bacteroides* and/or *Bifidobacterium*, further determining whether the subject has a decreased level of *Faecalibacterium, Clostridiales, Roseburia*, Ruminococcaceae, and/or *Eubacterium*, relative to a healthy control population; diagnosing the patient as having an increased risk of *P. aeruginosa* infection or chronic colonization if the patient has a decreased level of *Faecalibacterium, Clostridiales, Roseburia*, Ruminococcaceae, and/or *Eubacterium*, relative to a healthy control population.

In some embodiments, the method diagnoses or indicates the likelihood of *P. aeruginosa* infection or chronic colonization, or even permanent colonization. In some embodiments, the method aids in the determination of the time to onset of *P. aeruginosa* infection.

In some embodiments, the level of *Bacteroides, Bifidobacterium, Faecalibacterium, Clostridiales, Roseburia*, Ruminococcaceae, and/or *Eubacterium* is decreased relative to a healthy control population of the same age range.

In some embodiments, the level of *Bacteroides, Bifidobacterium, Faecalibacterium, Clostridiales, Roseburia*, Ruminococcaceae, and/or *Eubacterium* in a patient age 12 months or less is no greater than 8%, 7%, 6%, or 5% relative abundance. In some embodiments, the level of *Bacteroides, Bifidobacterium, Faecalibacterium, Clostridiales, Roseburia*, Ruminococcaceae, and/or *Eubacterium* in a patient age 4 months or less is no greater than 25%, 20%, 15%, 10%, 8%, 7%, 6%, or 5% relative abundance.

In some embodiments, the level of *Bacteroides, Bifidobacterium, Faecalibacterium, Clostridiales, Roseburia*, Ruminococcaceae, and/or *Eubacterium* is decreased relative to a healthy control population of the same age range.

In some embodiments, a method diagnosing the risk of pulmonary exacerbation in a patient having cystic fibrosis comprises determining whether the subject has a decreased level of *Streptococcus* and/or *Ruminococcus*, relative to a patient population without pulmonary exacerbation; diagnosing the patient as having an increased risk of pulmonary exacerbation if the patient has a decreased level of *Streptococcus* and/or *Ruminococcus*, relative to a patient population without pulmonary exacerbation. In some embodiments, the method diagnoses or indicates the likelihood of pulmonary exacerbation. In some embodiments, the method aids in the determination of the time to onset of pulmonary exacerbation.

In some embodiments, the level of *Streptococcus* and/or *Ruminococcus* in a patient aged 12 months or less is no greater than 50%, 40%, 30%, 20%, 15%, 12%, 10%, 8%, 7%, 6%, or 5% relative abundance.

III. TREATMENTS BASED ON DIAGNOSTIC INFORMATION

In some embodiments, knowing the profile of a patient's microbiome helps physicians choose how aggressively to treat a patient's CF and which treatments should be employed. A patient who has a poorer microbiome profile is more susceptible to disease-associated difficulties and should be treated more aggressively.

Diagnostic approaches as outlined in Section II above, titled Diagnostic Methods, may be used herein, followed, when appropriate with treatments according to this application and/or conventional CF treatments.

Specifically, diagnostic microbiome testing allows a clinician to determine the need of treatment (including preventive therapies) for cystic fibrosis or cystic fibrosis-associated clinical outcomes. Conventional treatments, therapies, or lifestyle changes may be administered or prescribed to a subject in need thereof.

In some embodiments, the method for treating cystic fibrosis or cystic fibrosis-associated clinical outcomes may include (i) administering an effective amount of the bacterial composition to a subject prior to, during, or subsequent to treatment with compounds or compositions including pancreatic enzyme replacement, probiotics, prebiotics, antibiotics, anti-inflammatory medications, mucus-thinning drugs, cystic fibrosis transmembrane conductance regulator (CFTR) function-improving medications, inhaled medications or bronchodilators; and/or (ii) prescribing physical therapy including postural drainage and chest physical therapy, and pulmonary rehabilitation to the subject.

1. Pancreatic Enzyme Replacement

The majority of individuals with cystic fibrosis suffer from pancreatic insufficiency where the individuals suffer from a lack of digestive enzymes made by their pancreas. In some embodiments, medications for exocrine pancreatic insufficiency, or pancreatic enzyme replacement therapy (PERT), may be employed. Pancreatic enzyme replacement therapy (PERT) involves taking digestive enzymes that assist the digestion of fat, carbohydrates and proteins-pancreatic enzyme products (PEPs).

Pancreatic enzyme products (PEPs) generally contain a mixture of the digestive enzymes amylase, lipase, and protease. In some embodiments, the medications for pancreatic enzyme replacement include, without limitation, pancreatin, pancrelipase, or other pancreatic enzyme substitute. In some embodiments, the medications for pancreatic enzyme replacement include, without limitation, CREON®, ZENPEP®, PANCREAZE®, ULTRESA®, VIOKACE®, PERTZYE®, Nutrizym, PANCREASE®, and Pancrex.

2. Prebiotics

Various prebiotics to promote the growth of the bacterial compositions described herein may be used. A prebiotic is usually a nondigestible carbohydrate or a sugar alcohol which is not degraded or absorbed in the digestive tract. The prebiotic is selected according to the bacterial compositions such that it supports the growth of the bacteria. Suitable prebiotics may include, e.g., oligosaccharides, particularly inulin, fructooligosaccharide (FOS), galactooligosaccharide (GOS), palatinoseoligosaccharide, soybean oligosaccharide, gentiooligosaccharide, xylooligomers, non-degradable starch, lactosaccharose, lactulose, lactitol, maltitol, polydextrose, pectin, or the like.

In some embodiments, such prebiotics include, without limitation, extracts of Gum arabic, leeks, asparagus, artichoke, chicory root, onion, garlic, kale, wheat bran, banana, oats, barley, various legumes, or the like. In some embodiments, prebiotics may include herbs. In some embodiments, such prebiotics may be commercially available prebiotic supplements.

3. Antibiotics

Various antibiotics may be used for the method for treating cystic fibrosis or cystic fibrosis-associated clinical outcomes as described herein. Such antibiotics may include, without limitation, penicillin (methicillin, oxacillin, naficillin, cabencillin, amoxicillin, clavulanic acid, cloxacillin, dicloxacillin, ticarcillin, piperacillin, mezlocillin, azlocillin, tazobactam); cephalosporins (cephalexin, cefdinir, cefprozil, ceflacor, cefuroxime, cefepime); sulfa antibiotics (sulfamethoxazole, trimethoprim); aminoglycosides (tobramycin, amikacin, gentamicin); erythromycin/sulfisoxazole; macrolides (erythromycin, clarithromycin, azithromycin); tetracyclines (tetracycline, doxycycline, minocycline, tigecycline); vancomycin; imipenem; meripenem; colistimethate); quinolones (ciprofloxacin, levofloxacin); aztreonam; linezolid. In some embodiments, one or more of GENTAK®, CETRAXAL®, CILOXAN®, CIPRO® in D5W, OTIPRIO®, CIPRO® XR (ciprofloxacin), ZITHROMAX® (azithromycin), AzaSite, ZMAX®, ZITHROMAX® TRI-PAK, ZITHROMAX® Z-Pak, CAYSTON®, AZACTAM®, MERREM®, FORTAZ®, TOBI® (tobramycin), KITA-BIS® Pak, BETHKIS®, and ZOSYN® is used.

4. Anti-Inflammatory Medications

Various anti-inflammatory medications to lessen the inflammatory responses (e.g., swelling in the airways of the lungs) may be employed for the method for treating cystic fibrosis or cystic fibrosis-associated clinical outcomes. Such anti-inflammatory medications may include, without limitation, corticosteroid, ibuprofen or other non-steroidal anti-inflammatory medications, anti-inflammatory cytokines, antibody or antigen binding fragment thereof to pro-inflammatory cytokine, antioxidants, protease inhibitors, membrane stabilizers. Further, such anti-inflammatory medications may include, without limitation, corticosteroid (fluticasone (XHANCE®) or prednisone (DELTASONE®, RAYOS®, Prednisone Intensol), ibuprofen, Anti-ICAM-1, anti-IL-8, anti-IL-17, IL-10, Interferon-γ, p38 Mitogen-activated protein kinase inhibitors, al-Protease inhibitor, CXCR2 antagonist, cyclosporine-A, DHA, EPI-hNE4, glutathione, hydroxychloroquine, 1-Arginine, LTB4 receptor antagonist (BIIL 284 BS), methotrexate, monocyte/neutrophil elastase inhibitor, montelukast, N-Acetylcysteine, omega-3-fatty acids, secretory leukoprotease inhibitor, Simvastatin, thiazolidinediones/pioglitazone, vitamins C, E, and β-carotene, and vitamin D.

5. Mucus-Thinning Drugs

Various mucus-thinning drugs to improve airway function may be employed for the method for treating cystic fibrosis or cystic fibrosis-associated clinical outcomes. The mucus-thinning drugs include, without limitations, hypertonic saline, dornase alfa (PULMOZYME®), and acetylcysteine (ACETADOTE®, NAC®, and CETYLEV®).

6. Medications that Improve Cystic Fibrosis Transmembrane Conductance Regulator (CFTR) Function Various medications that improve cystic fibrosis transmembrane conductance regulator (CFTR) function, the defective protein that causes cystic fibrosis, may be employed for the method for treating cystic fibrosis or cystic fibrosis-associated clinical outcomes. In some embodiments, such medications include, without limitation, at least one of ivacaftor, lumacaftor/ivacaftor (ORKAMBI®), and tezacaftor/ivacaftor (SYMDEKO®), or newly developed therapies as they are developed. In some such embodiments, such medications include, without limitation, at least one of ivacaftor, lumacaftor/ivacaftor (ORKAMBI®), and tezacaftor/ivacaftor (SYMDEKO®).

7. Bronchodilator/Inhaled Medications

Various inhaled medications may be employed for the method for treating cystic fibrosis or cystic fibrosis-associated clinical outcomes. In some embodiments, the inhaled medications include a bronchodilator that helps relax the muscles around the bronchial tubes may be employed. Such inhaled medications include, without limitation, at least one of albuterol or levabuterol.

In some embodiments, the inhaled medications include one or more of the aforementioned probiotics and antibiotics (e.g., inhaled antipseudomonal antibiotics). In some embodiments, such inhaled medications include inhaled steroidal anti-inflammatory medications, such as beclomethasone dipropionate (QVAR®), budesonide (PULMICORT®), budesonide/formoterol (SYMBICORT®), fluticasone (FLOVENT®), fluticasone inhaled powder (ARNUITY ELLIPTA®), fluticasone/salmeterol (ADVAIR®), mometasone (ASMANEX®), and mometasone/formoterol (DULERA®).

8. Physical Therapies/Other Procedures

Various physical therapies and other medical procedures may be prescribed to the subject along with the administration of the or compositions described in the present disclosure for the methods for treating cystic fibrosis or cystic fibrosis-associated clinical outcomes in a subject in need thereof.

The physical therapy may include prescribing postural drainage, chest physical therapy, or pulmonary rehabilitation. The postural drainage may be performed by getting into positions that make it easier for mucus to drain from the lungs. The chest physical therapy may include, without limitation, at least one of vibrating vest and chest wall oscillation. The pulmonary rehabilitation may include, without limitation, at least one of physical exercise, breathing techniques, and nutritional counseling.

IV. EXEMPLARY EMBODIMENTS

Exemplary Embodiment A

A1: In one aspect, the present disclosure provides a method of altering the intestinal microbiome in a patient diagnosed with cystic fibrosis comprising administering at least one of *Bifidobacterium* and/or *Bacteroides* to a patient and allowing the *Bifidobacterium* and/or *Bacteroides* to alter the intestinal microbiome. A2: In certain embodiments of A1, the method comprises administering both *Bifidobacterium* and *Bacteroides*. A3: In certain embodiments of A1 or A2, the method further comprises administering *Streptococcus*. A4: In certain embodiments of A1-A3, altering the intestinal microbiome treats cystic fibrosis or alleviates a symptom thereof. A5: In certain embodiments of A1-A4, altering the intestinal microbiome comprises reducing the risk of, severity of, or delaying the onset of pathogenic microbial infection, wherein the pathogenic microbial infection comprises *Staphylococcus aureus* infection, *Pseudomonas aeruginosa* infection, *Stenotrophomonas* infection, *Haemophilus influenzae* infection, nontuberculous mycobacterial (including but not limited to *Mycobacteria abcessus* or *Mycobacteria avium*) infection, *Burkholderia cepacia* complex infection, viral or fungal infection, or co-infections with multiple pathogens. A6: In certain embodiments of A1-A5, altering the intestinal microbiome comprises reducing the risk of, severity of, or delaying the onset of *P. aeruginosa* infection or chronic colonization. A7: In certain embodiments of A1-A6, altering the intestinal microbiome comprises reducing the risk of, severity of, or delaying pulmonary exacerbation. A8: In certain embodiments of A4, treating cystic fibrosis comprises reducing the risk of, severity of, or delaying cystic fibrosis-associated outcomes.

Exemplary Embodiment B

B1: In one aspect, the present disclosure provides a method for altering the intestinal microbiome in a subject having cystic fibrosis comprising administering at least one of *Streptococcus* and/or *Ruminococcus* to the subject and allowing the *Streptococcus* and/or *Ruminococcus* to alter the intestinal microbiome. B2: In certain embodiments of B1, altering the intestinal microbiome comprises reducing the risk of, severity of, or delaying pulmonary exacerbation.

Exemplary Embodiment C

C1: In one aspect, the present disclosure provides a method of treating a patient with cystic fibrosis comprising determining from a fecal sample whether the patient has a decreased level of *Bifidobacterium, Bacteroides, Faecalibacterium, Clostridiales, Roseburia, Ruminococcaceae, Eubacterium, Streptococcus*, and/or *Ruminococcus* relative to a healthy control population and (a) if it is determined that the patient has a decreased level of *Bifidobacterium, Bacteroides, Faecalibacterium, Clostridiales, Roseburia, Ruminococcaceae, Eubacterium, Streptococcus*, and/or *Ruminococcus* relative to a healthy control population administering an effective amount of cystic fibrosis therapy to the subject thereby treating cystic fibrosis, wherein the cystic fibrosis therapy comprises one or more of (i) at least one pancreatic enzyme replacement product; (ii) at least one probiotic; (iii) at least one prebiotic; (iv) at least one antibiotic; (v) at least one anti-inflammatory medication; (vi) at least one mucus-thinning drug; (vii) at least one cystic fibrosis transmembrane conductance regulator (CFTR) function-improving medication; and/or (viii) at least one bronchodilator or inhaled medication. C2: In certain embodiments of C1, the method of treating cystic fibrosis comprises altering the intestinal microbiome. C3: In certain embodiments of C1 or C2, the method of treating cystic fibrosis comprises reducing the risk of, severity of, or delaying the onset of *P. aeruginosa* infection or chronic colonization. C4: In certain embodiments of C1-C4, the method of treating cystic fibrosis comprises reducing the risk of, severity of, or delaying cystic fibrosis-associated outcomes. C5: In certain embodiments of C4, the cystic fibrosis-associated outcomes includes at least one of pulmonary exacerbation, infection or chronic colonization with *P. aeruginosa* or other pathogen, growth failure or diagnosis of failure to thrive, early all-cause hospitalization, nutritional malabsorbtion, gastrointestinal-related outcomes (including but not limited to small bowel bacterial overgrowth, decreased absorption of essential fats), and disease-associated changes in body mass index (BMI).

Exemplary Embodiment D

D1: In certain embodiments of A1-A8, B1-B2, or C1-C5, the patient is 0 days old to 3 years old, 0 days old to 2 years old, 0 days old to 18 months old, 1 week old to 12 months old, 3 months old to 9 months old, or 1 week old to 6 months old. D2: In certain embodiments of D1, the patient is 0 days old to 12 months old, 1 week old to 12 months old, 3 months old to 9 months old, or 1 week old to 6 months old.

Exemplary Embodiment E

E1: In certain embodiments of B1-B2 or C1-C5, the at least one pancreatic enzyme replacement product comprises pancreatin, pancrelipase, or other pancreatic enzyme substitutes. E2: In certain embodiments of B1-B2, C1-C5, or E1, the at least one probiotic comprises a microbial composition comprising at least one of *Bifidobacterium, Bacteroides, Faecalibacterium, Clostridiales, Roseburia, Ruminococcaceae, Eubacterium, Streptococcus*, and *Ruminococcus*. E3: In certain embodiments of B1-B2, C1-C5, or E1-E2, the at least one prebiotic comprises at least one of oligosaccharides, inulin, fructooligosaccharide (FOS), galactooligosaccharide (GOS), palatinoseoligosaccharide, soybean oligosaccharide, gentiooligosaccharide, xylooligomers, non-degradable starch, lactosaccharose, lactulose, lactitol, maltitol, polydextrose, and pectin. E4: In certain embodiments of B1-B2, C1-C5, or E1-E3, the method further comprises prescribing postural drainage, chest physical therapy, and/or pulmonary rehabilitation. E5: In certain embodiments of E4, the chest physical therapy comprises at least one of vibrating vest and chest wall oscillation. E6: In certain embodiments of E4, the pulmonary rehabilitation includes at least one of physical exercise, breathing techniques, and nutritional counseling. E7: In certain embodiments of B1-B2, C1-C5, or E1-E6, the at least one antibiotic is chosen from at least one of penicillin (methicillin, oxacillin, naficillin, cabencillin, amoxicillin, clavulanic acid, cloxacillin, dicloxacillin, ticarcillin, piperacillin, mezlocillin, azlocillin, tazobactam); cephalosporins (cephalexin, cefdinir, cefprozil, ceflacor, cefuroxime, cefepime); sulfa antibiotics (sulfamethoxazole, trimethoprim); aminoglycosides (tobramycin, amikacin, gentamicin); erythromycin/sulfisoxazole; macrolides (erythromycin, clarithromycin, azithromycin); tetracyclines (tetracycline, doxycycline, minocycline, tigecycline); vancomycin; imipenem; meripenem; colistimethate); quinolones (ciprofloxacin, levofloxacin); aztreonam; linezolid. E8: In certain embodiments of B1-B2, C1-C5, or E1-E7, the at least one anti-inflammatory medication is chosen from at least one of corticosteroid, ibuprofen, non-steroidal anti-inflammatory medication, anti-inflammatory cytokines, antibody or antigen binding fragment thereof to pro-inflammatory cytokine, antioxidants, protease inhibitors. E9: In certain embodiments of B1-B2, C1-C5, or E1-E8, the at least one cystic fibrosis transmembrane conductance regulator (CFTR)-improving medication is at least one of ivacaftor, lumacaftor/ivacaftor, and tezacaftor/ivacaftor. E10: In certain embodiments of B1-B2, C1-C5, or E1-E9, the at least one mucus-thinning drug is chosen from at least one of hypertonic saline, dornase alfa, and acetylcysteine. E11: In certain embodiments of B1-B2, C1-C5, or E1-E10, the at least one bronchodilator comprises albuterol or levabuterol. E12: In certain embodiments of B1-B2, C1-C5, or E1-E11, the method of treating cystic fibrosis comprises the method of any one of A1-A10. E13: In certain embodiments of A3-A10, B1-B2, C1-C5, or E1-E12, the bacteria of *Streptococcus* comprises at least one chosen from *S. bovis, S. gallolyticus, S. macedonicus, S. alactolyticus, S. vestibularis, S. salivarius, S. mitis, S. parasanguinis, S. lutetiensis, S. equinus* and *S. infantarius*. E14: In certain embodiments of B1-B2, C1-C5, or E1-E13, the level of *Bifidobacterium* and/or *Bacteroides* is decreased relative to a healthy control population of the same age range. E15: In certain embodiments of B1-B2, C1-C5, or E1-E14, the biological (including, but not limited to fecal) sample is obtained from a patient age 2 or less, age 18 months or less, age 12 months or less, age 6 months or less, or age 4 months of less. E16: In certain embodiments of B1-B2, C1-C5, or E1-E15, 16S rRNA sequencing is used to determine the relative abundance of intestinal microbes in the biological (including, but not limited to fecal) sample. E17: In certain embodiments of B1-B2, C1-C5, or E1-E16, the level of *Bifidobacterium* in a patient age of 12 months or less is no greater than 8%, 7%, 6%, or 5% relative abundance. E18: In certain embodiments of B1-B2, C1-C5, or E1-E17, the level of *Bifidobacterium* in a patient aged 4 months or less is no greater than 25%, 20%, 15%, 10%, 8%, 7%, 6%, or 5% relative abundance. E19: In certain embodiments of B1-B2, C1-C5, or E1-E18, the level of *Bacteroides* in a patient aged 12 months or less is no greater than 15%, 12%, 10%, 8%, 7%, 6%, 5%, or 4% relative abundance. E20: In certain embodiments of B1-B2, C1-C5, or E1-E19, the level of *Bacteroides* in a patient aged 4 months or less is no greater than 20%, 15%, 12%, 10%, 8%, 7%, 6%, or 5% relative abundance. E21: In certain embodiments of A3-A10, B1-B2, C1-C5, or E1-E20, the level of *Streptococcus* in a patient aged 12 months or less is no greater than 20%, 15%, 12%, 10%, 8%, 7%, 6%, or 5% relative abundance. E22: In certain embodiments of B1-B2, C1-C5, or E1-E21, the patient has decreased levels of *Faecalibacterium, Eubacterium* or *Roseburia*. E23: In certain embodiments of B1-B2, C1-C5, or E1-E22, the patient has increased levels of *Faecalibacterium*, Clostridiales, Clostridiaceae, *Veillonella, Streptococcus, Clostridium*, and/or Enterobacteriacea. E24: In certain embodiments of B1-B2, C1-C5, or E1-E23, the levels of *Faecalibacterium*, Clostridiales, Clostridiaceae, *Veillonella, Streptococcus, Clostridium*, and/or Enterobacteriacea are increased relative to a healthy control population of the same age range. E25: In certain embodiments of B1-B2, C1-C5, or E1-E24, the level of *Bifidobacterium* in a patient aged 4 months or less is no greater than 30%, 25%, 20%, 15%, 12%, 10%, 8%, 7%, 6%, or 5% relative to the level of *Bifidobacterium* in a healthy control population of the same range. E26: In certain embodiments of B1-B2, C1-C5, or E1-E25, the level of *Bacteroides* in a patient aged 4 months or less is no greater than 30%, 25%, 20%, 15%, 12%, 10%, 8%, 7%, 6%, or 5% relative to the level of *Bacteroides* in a healthy control population of the same range. E27: In certain embodiments of B1-B2, C1-C5, or E1-E26, the level of *Bifidobacterium* in a patient aged 12 months or less is no greater than 30%, 25%, 20%, 15%, 12%, 10%, 8%, 7%, 6%, or 5% relative to the level of *Bifidobacterium* in a healthy control population of the same range. E28: In certain embodiments of B1-B2, C1-C5, or E1-E27, the level of *Bacteroides* in a patient aged 12 months or less is no greater than 30%, 25%, 20%, 15%, 12%, 10%, 8%, 7%, 6%, or 5% relative to the level of *Bacteroides* in a healthy control population of the same range.

Exemplary Embodiment F

F1: In one aspect, the present disclosure provides a method of diagnosing the risk of *P. aeruginosa* infection or chronic colonization, or pulmonary exacerbation, in a patient having cystic fibrosis comprising: (a) determining from a biological sample from the patient whether the patient has a decreased level of *Bifidobacterium* and/or *Bacteroides* by comparing the level of *Bifidobacterium* and/or *Bacteroides* in the patient with the level of *Bifidobacterium* and/or *Bacteroides* in a healthy control population; (b) diagnosing the patient as having an increased risk of *P. aeruginosa* infection or chronic colonization, or pulmonary exacerbation, if the patient has a decreased level of *Bifidobacterium* and/or *Bacteroides* compared to the healthy control population. F2: In certain embodiments of F1, the biological sample is a fecal sample. F3: In certain embodiments of F1 or F2, the method diagnoses the likelihood of *P. aeruginosa* infection or chronic colonization, or pulmonary exacerbation.

Exemplary Embodiment G

G1: In one aspect, the present disclosure provides a method of reducing a pro-inflammatory response and/or promoting an anti-inflammatory response in a patient having cystic fibrosis, the method comprising administering at least one of *Bifidobacterium* and/or *Bacteroides* to the patient, wherein prior to said administration a sample from the patient has been tested to determine a level of *Bifidobacterium* and/or *Bacteroides*. G2: In certain embodiments of G1, the pro-inflammatory response is a systemic pro-inflammatory response. G3: In certain embodiments of G1, the pro-inflammatory response comprises production and/or expression of pro-inflammatory mediators (e.g., IL-8). G4: In certain embodiments of G1, the anti-inflammatory response is a systemic anti-inflammatory response. G5: In certain embodiments of G1, the anti-inflammatory response comprises production and/or expression of anti-inflammatory mediators (e.g., IL-10).

Exemplary Embodiment H

H1: In one aspect, the present disclosure provides a method of preventing, delaying the onset, reducing the severity, and/or reducing the duration of an infection by a pathogen, or an exacerbation thereof, in a patient in need thereof, the method comprising administering to the patient at least one of *Bifidobacterium* and/or *Bacteroides* to the patient, wherein prior to said administration a sample from the patient has been tested to determine a level of *Bifidobacterium* and/or *Bacteroides*. H2: In certain embodiments of H1, the pathogen is *P. aeruginosa*.

Exemplary Embodiment I

I1: In certain embodiments of G1-G5 or H1-H2, the patient is a pediatric patient. I2: In certain embodiments, of I2 the patient is 0 days old to 3 years old, 0 days old to 2 years old, 0 days old to 18 months old, 1 week old to 12 months old, 1 week old to 6 months old. I3: In certain embodiments of G1-G5, H1-H2, or I1-I2, the sample is a fecal sample Exemplary Embodiment J J1: A composition comprising (a) at least one of at least one of *Bifidobacterium* and/or *Bacteroides*; or (b) at least one of *Streptococcus* and/or *Ruminococcus*, wherein the composition is for use in the treatment of cystic fibrosis. J2: The composition of J1, wherein the composition comprises at least one of *Bifidobacterium* and/or *Bacteroides*. J3: The composition of J2, wherein the composition comprises both *Bifidobacterium* and *Bacteroides*. J4: The composition of J2-J3, wherein the composition further comprises *Strepto-*

*coccus*. J5: The composition of J1, wherein the composition comprises at least one of *Streptococcus* and/or *Ruminococcus*. J6: The composition of J1-J5, wherein composition is suitable for oral or nasogastric administration.

V. DEFINITIONS AND SUPPORTING INFORMATION

The terms "gut microbiota" or "gut microbiome" or "intestinal microbiota" or "intestinal microbiome" are used interchangeably and refer to the microorganisms that colonize the gastrointestinal tract of a human. As used herein, the terms "microbe" or "microorganism" encompass both prokaryotic organisms including bacteria and archaea, and eukaryotic organisms, including fungi, other single-celled eukaryotes, and viruses, present in mammalian microbiota.

By "modifying the intestinal microbiome", "altering the intestinal microbiome", "improving the gut microbiome" or "improving the intestinal microbiome" is meant any change, either increase or decrease, of the intestinal microbiota or microbiome in a subject. In some embodiments, modifying, altering, improving the intestinal microbiota includes increasing or decreasing the levels of specific bacteria, such as in the gastrointestinal tract of a subject. In some embodiments, modifying, altering, improving the intestinal microbiota includes increasing the levels of the bacteria described herein in the gastrointestinal tract of a subject.

By "increase," "increasing", "decrease" or "decreasing" is meant a change in the levels of specific bacteria in the gastrointestinal tract of a subject. An increase or decrease may include a change of any value from 10% and 100%, or of any value from 30% and 60%, or over 100%, for example, a change of about 10%, 20% 30%, 40%, 50%, 60%, 70%, 80%, 90%, 95% or more, when compared to a control. In some embodiments, the increase or decrease may be a change of about 1-fold, 2-fold, 5-fold, 10-fold, 100-fold, or more, when compared to a control.

Specific taxa and changes in microbiota discussed herein can be detected using various methods, including without limitation quantitative PCR (qPCR) or high-throughput sequencing (e.g., shotgun metagenome sequencing) methods which detect over- and under-represented genes in the total bacterial population (e.g., screening of microbial 16S ribosomal RNAs (16S rRNA)), or transcriptomic or proteomic studies that identify lost or gained microbial transcripts or proteins within total bacterial populations, or metabolomics, as previously described (e.g., Madan et al., mBio 2012; Hoen et al., J Pediatr, 2015; Filkins et al., J Bacteriol, 2012; Price et al., Microbiome, 2013; Gifford et al., J Cyst Fibros, 2014; Hampton et al., Microbiome, 2014).

As used herein, the term "16S rRNA sequencing" refers to the sequencing of 16S ribosomal RNA (rRNA) gene sequences by using primers such as universal primers and/or species-specific primers to identify the bacteria present in a sample. 16S rRNA genes contain both highly conserved sites and hypervariable regions that can provide species-specific signature sequences useful for identification of bacteria. Such universal primers are well known in the art.

As used herein, the term "operational taxonomic unit" or "OTU" refers to classification of microbes within the same, or different, OTUs using techniques, as described herein, or known in the art. OTU refers to a terminal leaf in a phylogenetic tree and is defined by a nucleic acid sequence, e.g., the entire genome, or a specific genetic sequence, and all sequences that share sequence identity to this nucleic acid sequence at the level of species. The specific genetic sequence may be the 16S rRNA sequence or a portion of the 16S rRNA sequence or it may be a functionally conserved housekeeping gene found broadly across the eubacterial kingdom. In 16S rRNA embodiments, OTUs that share >97% average nucleotide identity across the entire 16S rRNA or some variable region of the 16S rRNA are considered the same OTU.

As used herein, "cystic fibrosis-associated clinical outcomes" or "disease progression in cystic fibrosis" may include pulmonary exacerbation, infection or chronic colonization with *P. aeruginosa* or other pathogen, growth failure or diagnosis of failure to thrive, early all-cause hospitalization, nutritional malabsorbtion, gastrointestinal-related outcomes such as small bowel bacterial overgrowth, decreased absorption of essential fats, and/or disease-associated changes in body mass index (BMI).

As used herein, the term "pulmonary exacerbation" generally entails acute worsening of symptoms (e.g., increased cough, sputum production, shortness of breath) accompanied by an acute decrease in lung function and often resulting in therapeutic interventions including antibiotics and/or hospitalization.

The terms "treatment," "treating" or "therapy" encompass prophylactic, palliative, therapeutic, and nutritional modalities of administration of the bacterial compositions described herein. Accordingly, treatment includes amelioration, alleviation, reversal, or complete elimination of one or more of the symptoms in a subject diagnosed with, or known to have, cystic fibrosis, or cystic fibrosis-associated clinical outcomes (as discussed in the definition of "cystic fibrosis-associated clinical outcomes" above including, but not limited to, pulmonary exacerbation, or *P. aeruginosa* infection), or be considered to derive benefit from the alteration of intestinal microbiota. Such treatment also includes treating gastrointestinal (GI) outcomes such as prevention of small bowel bacterial overgrowth, improvement in absorption of essential fats, decrease in growth failure.

In the context of the present application, a "treatment" is a procedure which alleviates or reduces the negative consequences of cystic fibrosis. Any treatments or potential treatments can be used in the context herein. A treatment is not necessarily curative, and may reduce the symptom or effect of cystic fibrosis by a certain percentage over an untreated subject. The percentage reduction or diminution can be from 10% up to 20, 30, 40, 50, 60, 70, 80, 90, 95, 99 or 100%. "Treatment" also includes methods or preventing, inhibiting the development, or reducing the risk of cystic fibrosis, unless otherwise stated. It will be appreciated that, although not precluded, treating cystic fibrosis or the risk of developing cystic fibrosis does not require that the disease or the risk be completely eliminated.

As used herein, "inhibiting the development of," "reducing the risk of," "prevent," "preventing," and the like refer to reducing the probability of developing a symptom, condition, or disorder in a patient who may not yet have a symptom, condition, or disorder, but may have a genetic predisposition to developing it. For example, "preventing" includes inhibiting or reducing the probability of developing pulmonary exacerbation, or *P. aeruginosa* infection or chronic colonization, or any other cystic fibrosis-associated clinical outcomes. As used herein, "at risk," "susceptible to," or "having a genetic predisposition to," refers to having a propensity to develop a symptom, condition, or disorder. For example, a patient may have been diagnosed as having cystic fibrosis, but may not yet have respiratory exacerbation or infection with *P. aeruginosa*.

As used herein "patient" or "subject" refers to any human being receiving or who may receive medical treatment.

These terms also include mammals. Mammals include, but are not limited to, domesticated animals (e.g., cows, sheep, cats, dogs, and horses), primates (e.g., humans and non-human primates such as monkeys), rabbits, and rodents (e.g., mice and rats). In some embodiments, the subject is a patient. In some embodiments, the subject may be a human infant with a family history of cystic fibrosis. The subject may be an infant, such as a human infant one year old or less, or three months old or less. In some embodiments, the subject may be a human infant at any age from 1 day to 350 days old, such as 1 day, 10 days, 20 days, 30 days, 40 days, 50 days, 60 days, 70 days, 80 days, 90 days, 100 days, 110 days, 120 days, 130 days, 140 days, 150 days, 160 days, 170 days, 180 days, 190 days, 200 days, 210 days, 220 days, 230 days, 240 days, 250 days, 260 days, 270 days, 280 days, 290 days, 300 days, 310 days, 320 days, 330 days, 340 days, 350, 365 days old. In some embodiments, the subject may be a human infant of 0 days old to 3 years old, 0 days old to 2 years old, 0 days old to 18 months old, 1 week old to 12 months old, 1 week old to 6 months old.

The subject may be suspected of having or at risk for cystic fibrosis-associated clinical outcomes (including pulmonary exacerbation, or *P. aeruginosa* and other pathogenic microbial infection or chronic colonization), be diagnosed with such cystic fibrosis-associated clinical outcomes, or be a control subject that is confirmed to not have any cystic fibrosis-associated clinical outcomes. Diagnostic methods for the cystic fibrosis-associated clinical outcomes, and the clinical delineation of such diagnoses are known to those of ordinary skill in the art.

The term "about" means a numeric value, including, for example, whole numbers, fractions, and percentages, whether or not explicitly indicated. The term "about" refers generally to a range of numerical values (e.g., ±5 to 10% of the recited range) that one of ordinary skill in the art would consider equivalent to the recited range (e.g., having the same function or result). When terms such as "at least" and "about" precede a list of numerical values or ranges, the terms modify all of the values or ranges provided in the list. In some instances, the term "about" may include numerical values that are rounded to the nearest significant figure.

As used herein "diagnosis" or "identifying a patient having" refers to a process of determining if an individual is afflicted with, or has a predisposition or is at risk to develop, a condition, disorder, or symptom, e.g., such as pulmonary exacerbation, cystic fibrosis-associated clinical outcomes, *P. aeruginosa* infection or colonization, and/or other condition, disorder, or symptom associated with worsening disease progression and/or earlier mortality.

Although certain embodiments and advantages have been described in detail, it should be understood that various changes, substitutions and alterations can be made herein without departing from the spirit and scope as defined in the appended claims.

Embodiments will be further illustrated in the following Examples which are given for illustration purposes only and are not intended to limit the application in any way.

EXAMPLES

Example 1-1. The Intestinal Microbial Communities of Infants with CF and Healthy Controls Over the First Year of Life In this Example, as a surrogate for the intestinal communities, stool samples from patients with CF and healthy controls at 4 months and 1 year of age were analyzed, utilizing the Dartmouth Cystic Fibrosis Infant and Children's Cohort compared with a subset of healthy infants from the New Hampshire Birth Cohort Study. Using these two cohorts, the differences between the intestinal microbiota of patients with CF and healthy controls were characterized over the first year of life, both to understand the differences in the microbiota associated with the intestinal tract in these two populations beginning in infancy, as well as to determine a link between intestinal microbiota and airway disease outcomes.

A. Patient Population

Institutional review board approval was obtained from the Center for the Protection of Human Subjects at Dartmouth College with yearly renewal of the approval. Parents of all study subjects provided written informed consent for the participation of their children in the study. Cystic fibrosis patients under 1 month of age were eligible for enrollment into the Dartmouth Infant and Children's Cystic Fibrosis Birth Cohort if they had a confirmed CF diagnosis and would be receiving regular care at the Dartmouth-Hitchcock Medical Center affiliated clinics in Lebanon, NH or Manchester, NH, as explained in Hoen et al., 2015. Healthy controls (i.e., patients without cystic fibrosis) were obtained from the New Hampshire Birth Cohort Study. Subjects in the New Hampshire Birth Cohort Study were enrolled prenatally as described in Madan et al., 2016. Stool samples and health data, including delivery mode, feeding, and antibiotics usage were collected prospectively at multiple time points for all study participants. Both cohorts continue to enroll subjects and collect samples.

Samples from 14 patients with CF and 20 healthy controls at 4 months were analyzed and samples from 13 patients with CF and 45 healthy controls at 1 year were analyzed. Of the patients with CF, 8 patients were common between 4-month and 1-year samples, thus 6 out of 14 patients at 4 months and 5 out of 13 patients at 1 year were unique. The healthy controls were randomly selected based on the availability of stool samples from a larger cohort of children recruited through the New Hampshire Birth Cohort Study. There is no overlap between the cohort of healthy children analyzed at 4 months and 1 year.

B. Analysis of Microbial Populations in Stool

Stool samples were collected from patients and stored frozen until processing. DNA was extracted from stool samples with the MoBio Powersoil bacterial DNA isolation kit and the Zymo Fecal DNA mini kit per manufacturer's instructions. Illumina targeted sequencing of the V4-V5 hypervariable region of the 16S rRNA gene was performed at the Marine Biological Laboratory in Woods Hole, Massachusetts, as reported previously (e.g., Madan et al., mBio 2012; Hoen et al., J Pediatr, 2015; Filkins et al., J Bacteriol, 2012; Price et al., Microbiome, 2013; Gifford et al., J Cyst Fibros, 2014; Hampton et al., Microbiome, 2014). The 16S rRNA gene sequence reads for patients with CF and healthy controls were collapsed into OTUs for each sample with the QIIME pipeline using the function pick_open_reference_otus (see FIG. 1). All subsequent analyses were performed in R version 3.3.3.

C. Statistical Analyses

Differences in the microbial profiles of stool samples from 14 patients with CF and 20 healthy controls at 4 months and 13 patients with CF and 45 healthy controls at 1 year were analyzed using Generalized Unifrac Distances. Distances were visualized using PCoA plots and the significance of clustering was determined through PERMANOVA. Within sample diversity was determined using the Shannon Diversity Index as calculated in the phyloseq R package function estimate_richness. Significant differences in the relative abundance of individual taxa were determined with a Wilcoxon rank sum test and verified with generalized linear models. Longitudinal data was analyzed using a mixed effects model to account for repeated measures and the Kenward-Roger method was used to approximate degrees of freedom and obtain p-values. Bonferroni correction was used to adjust for multiple testing.

Figure 2A:
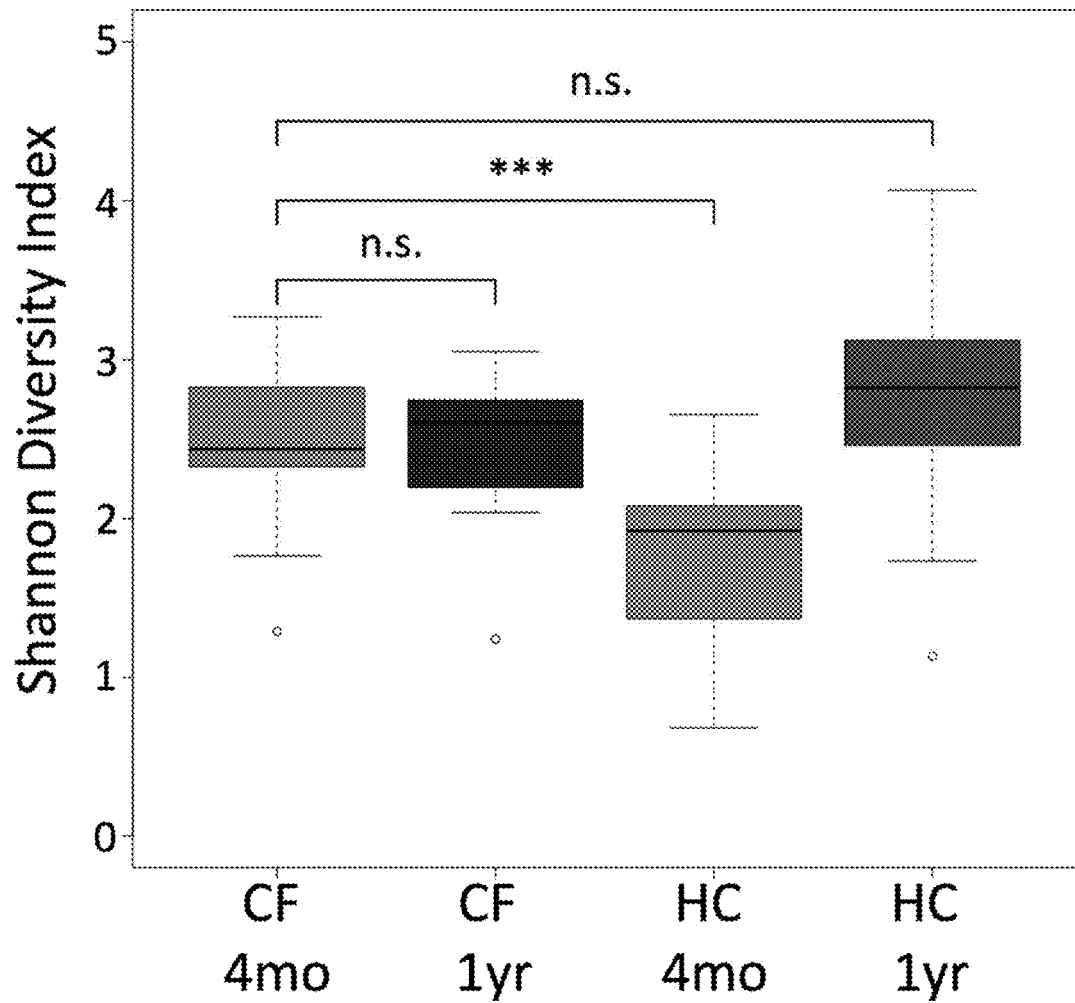
FIG. 2A shows comparison of the alpha diversity between patients with CF and healthy controls at 4 months and 1 year old. Using the Shannon diversity of CF samples at 4 months of age as the reference group, samples from 1-year old patients with CF were not significantly different from samples collected from 4-month old patients with CF (p=0.87). Samples collected for 4-month healthy controls had significantly lower alpha diversity than patients with CF at the same age (p=0.00025). While there is a trend toward increased diversity for healthy controls at 1-year old compared to patients with CF, this trend did not reach significance (p=0.091).
Figure 2B:
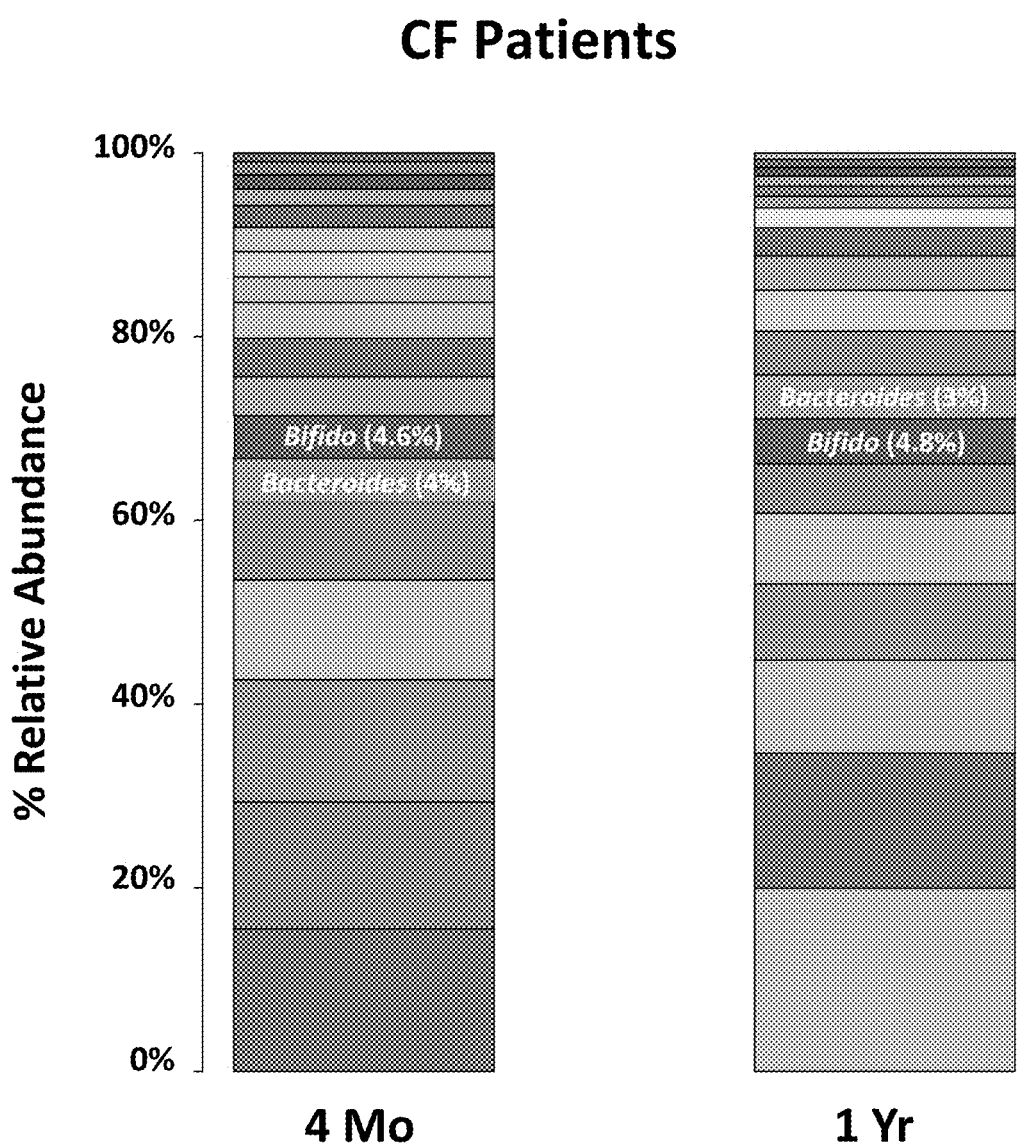
FIGS. 2B and 2C provide details of the relevant abundance of the top twenty OTUs in intestinal microbiomes of patients with CF and healthy controls respectively. Stacked bar plots represent OTUs from samples at 4 months of age and at 1 year of age. Each OTU is represented by the same color legend as in FIG. 1.
Figure 2C:
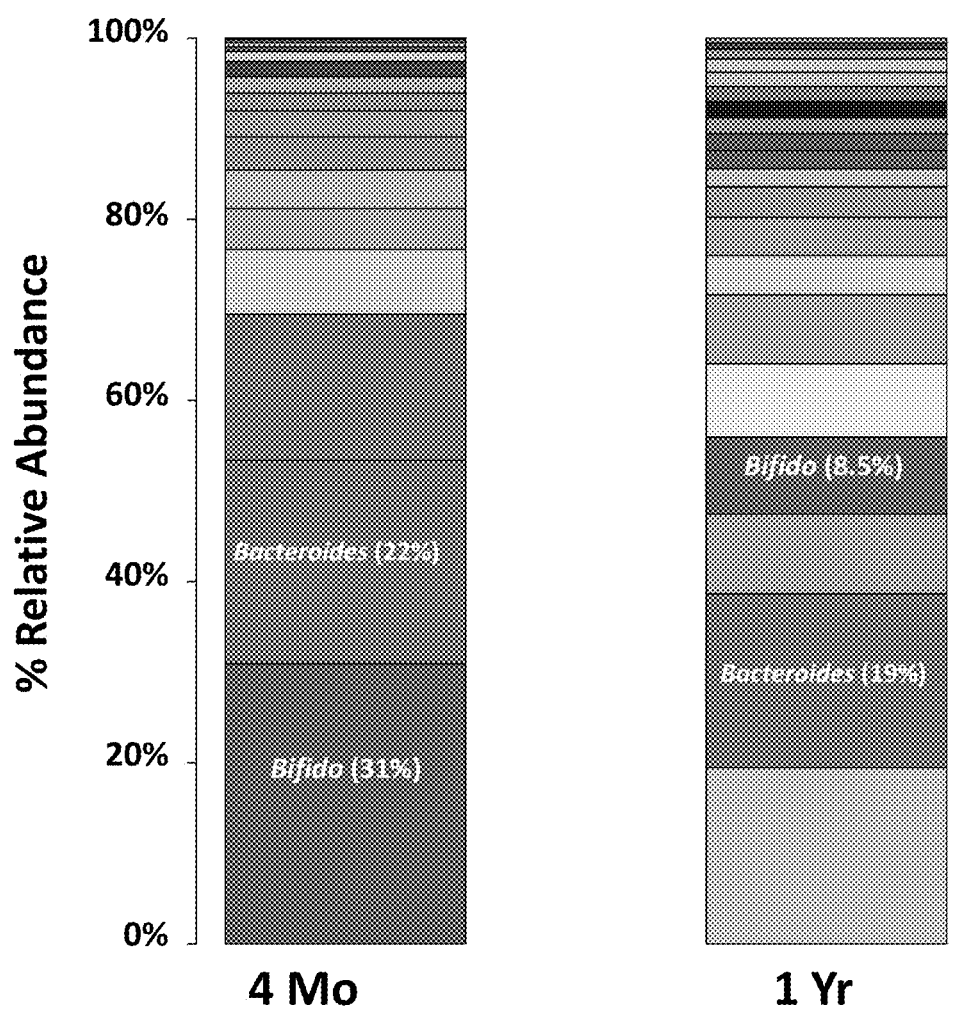

D. The Alpha Diversity of Stool Communities is Altered in Infants with CF in the First Year of Life Disease states are often associated with reduced microbial community diversity, including in CF. To examine the impact of CF on community (alpha) diversity, the Shannon Diversity Index (SDI) for infants with CF and healthy controls were analyzed at 4 months and 1 year of age for the microbial communities. As shown in FIG. 2A, at 4 months, the diversity of the microbial community in the stool of infants with CF was significantly higher than that of healthy infants ($p=<<0.001$). The infants with CF did not show a change in diversity at 1 year compared to 4 months, while in the healthy controls the diversity showed a significant increase to a level not significantly different from the diversity in the stool samples of infants with CF at 4 months and 1 year (FIG. 2A ($p=0.091$, using a generalized linear model); also compare FIG. 2B and FIG. 2C). These data indicate a significant difference in the microbial diversity associated with the stool of infants with CF versus healthy infants as early as 4 months of age.

Figure 3A:
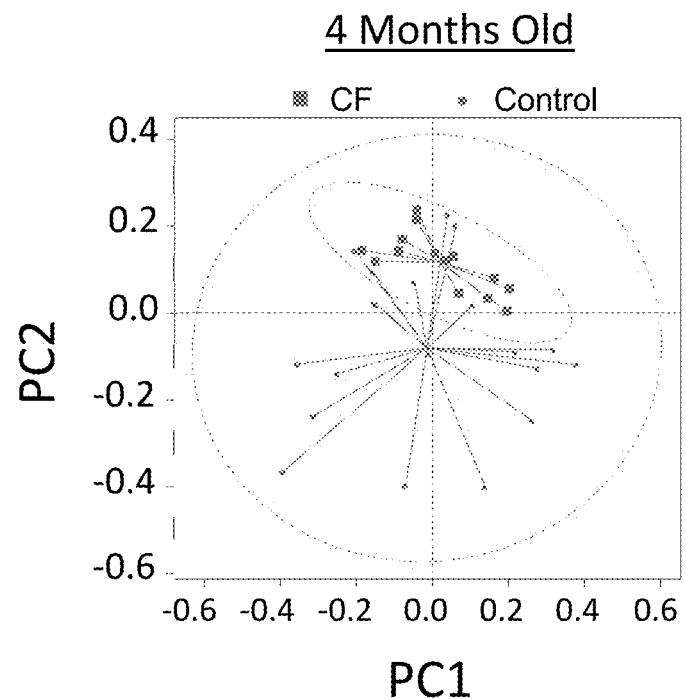
FIGS. 3A-3E show comparison of the beta diversity between patients with CF and healthy controls at 4 months of age and at 1 year of age. PCoA plots were generated from Generalized UniFrac distances between samples.

Example 1-2. The Intestinal Microbial Communities of Infants with CF Differ from Healthy Controls Over the First Year of Life The beta diversity (microbial community composition) of the infants with CF were analyzed in comparison to the healthy controls to find (1) whether the similar alpha diversity of patients with CF at 4 months and 1 year indicates a similar community composition among these samples; and (2) whether the similar alpha diversity among patients with CF and healthy controls at 1 year reflects similar community composition (beta diversity). The different alpha diversity measure of patients with CF and healthy controls at 4 months is reflected by a significant difference in beta diversity (FIG. 3A; PERMANOVA of generalized Unifrac distances; $p=0.002$). While the alpha diversity of healthy controls and patients with CF is not different at 1 year, these stool samples showed a significant difference in beta diversity (FIG. 3B; PERMANOVA of generalized Unifrac distances; $p=0.001$).

Figure 3B:
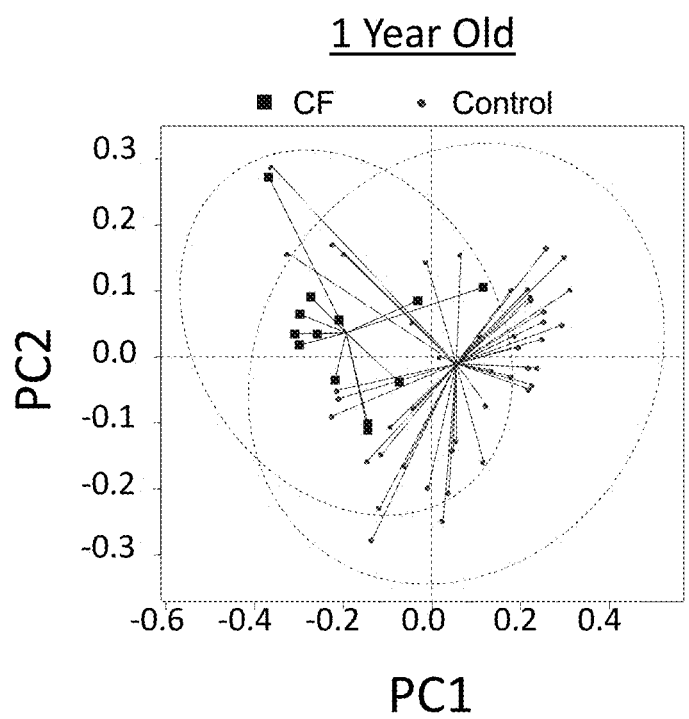
Figure 3C:
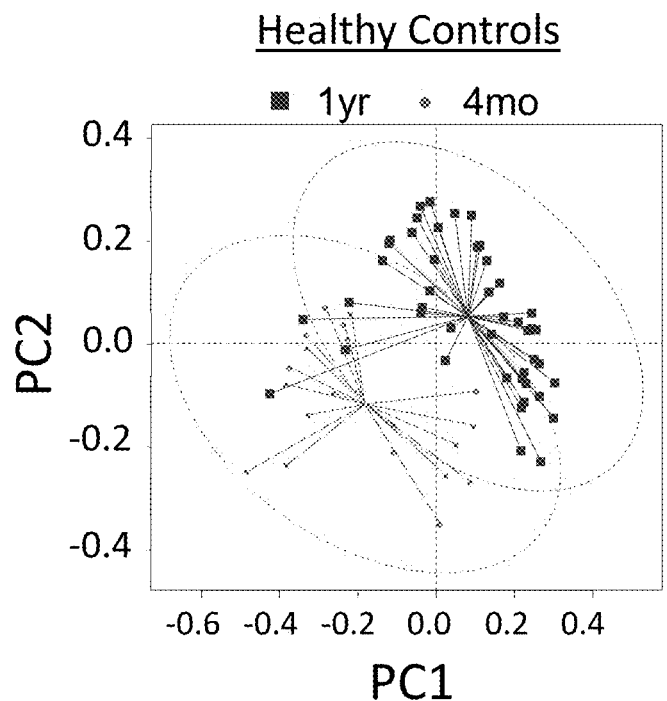
Figure 3D:
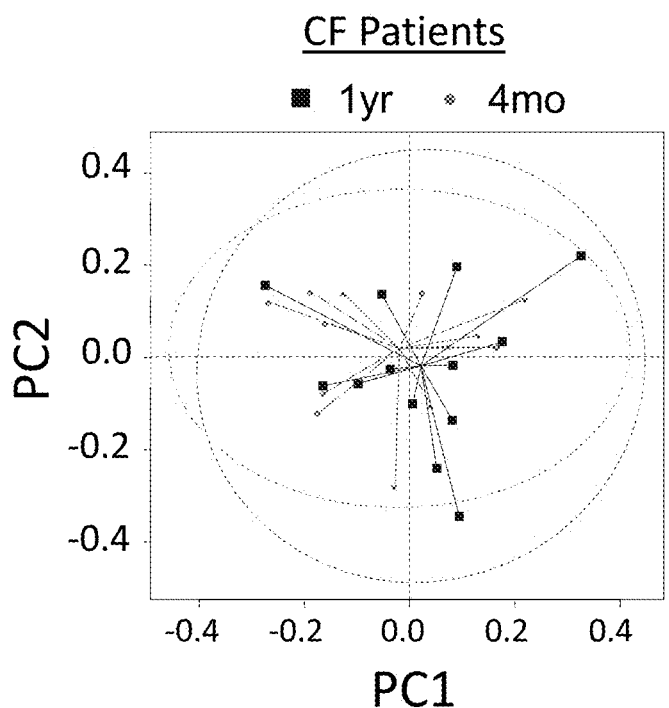
Figure 3E:
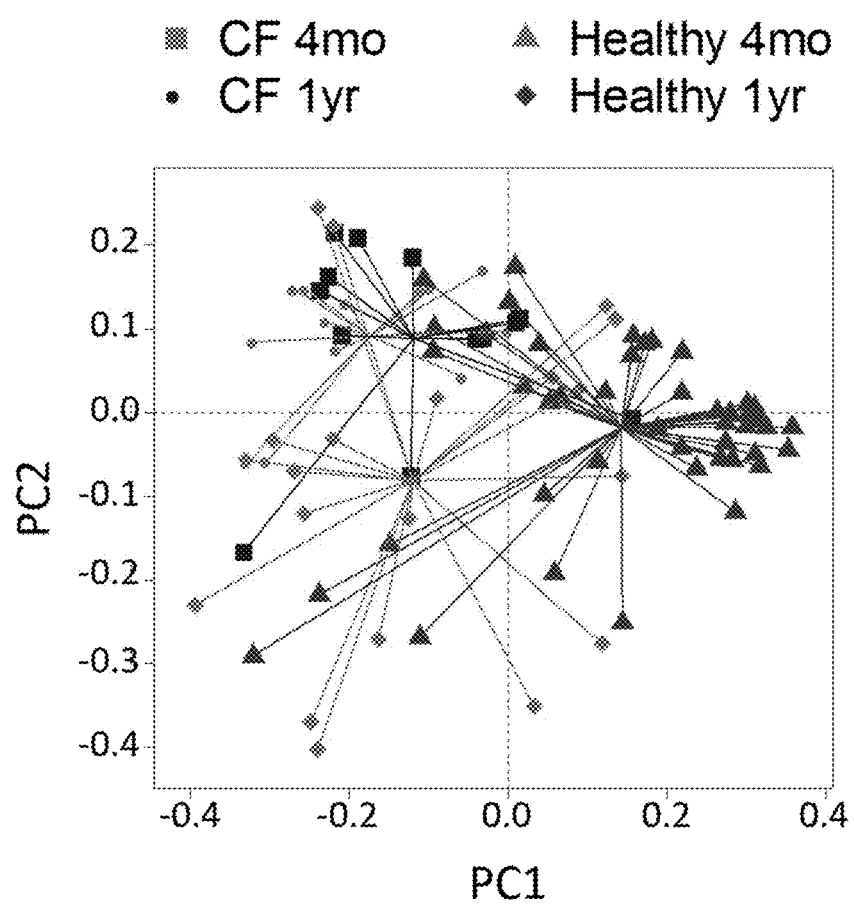

Consistent with the significant difference in alpha diversity for healthy children at 4 months and 1 year, there is a significant difference in beta diversity between these samples (FIG. 3C; PERMANOVA of generalized Unifrac distances; $p=0.001$). For infants with CF, the similar alpha diversity at 4 months and 1 year is also reflected by the clustering of communities, with no significant difference in beta diversity (FIG. 3D; PERMANOVA of generalized Unifrac distances; $p=0.396$). These data show that children with CF had an intestinal microbiome community that is distinct from the healthy controls as early as 4 months. Moreover, despite a similarity of alpha diversity by 1 year between CF and healthy cohorts, the composition of the intestinal communities (beta diversity) in these cohorts was distinct at 1 year. Furthermore, the altered intestinal microbiome community of these infants with CF did not change markedly across the first year of life. As indicated, the similar alpha diversity of patients with CF at 4 months and healthy children at 1 year is not reflected by a similar microbial community, that is, the beta diversity of these samples is significantly different (see FIG. 3E).

Example 1-3. Alterations in the Beta Diversity of Stool of Infants with CF Driven by Changes in a Small Group of Microbes at 4 Months of Age To further explore the basis of the differences in beta diversity between patients with CF and healthy controls, differences in individual OTUs, assigned at the genus level, when possible, or otherwise at the next lowest taxonomic level, were analyzed. Selecting the top 25 OTUs in each data set resulted in a collection of microbes that almost perfectly overlapped, and captured the top 20 OTUs for each cohort in terms of relative abundance (FIG. 4A).

Figure 4A:
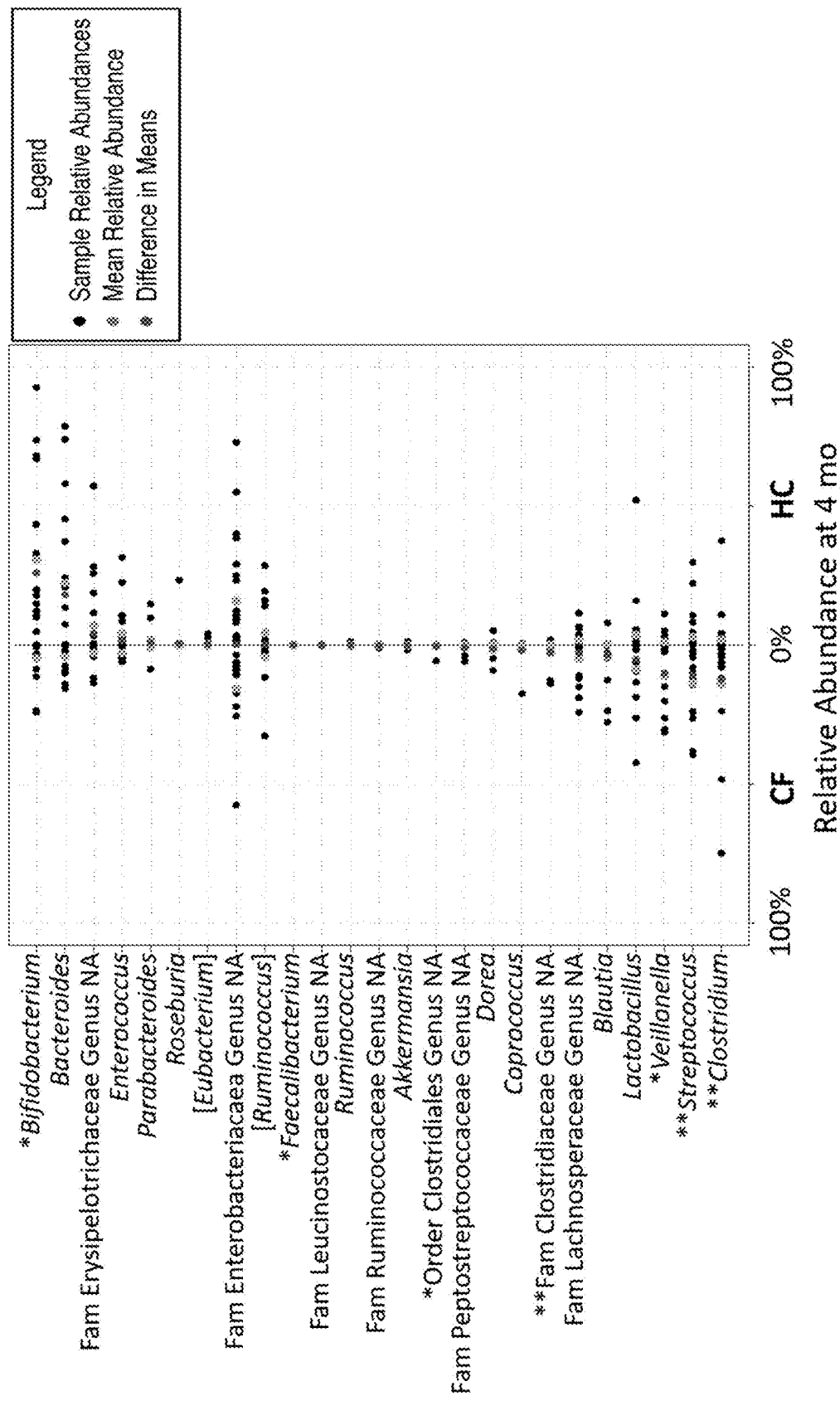
FIGS. 4A and 4B show comparison of relative abundance of top 25 OTUs present in samples from patients with CF and healthy controls. *, , and * indicate significant differences by the Wilcoxon rank-sum test after Bonferroni correction (p=0.001, p=0.01, and p=0.05, respectively). Abbreviations: Fam, family; NA, not assigned.

From a Wilcoxon rank-sum test to compare the relative abundance of OTUs present at 4 months, *Bifidobacterium* was significantly higher in the healthy controls while *Streptococcus*, *Veillonella*, and *Clostridium* were significantly higher in patients with CF (FIG. 4A). Three lower abundance groups (~1% relative abundance for most samples) were also significantly different: *Faecalibacterium* and two unassigned genera in the order Clostridiales (FIG. 4A). None of the other nineteen most abundant OTUs were significantly different at 4 months between patients with CF and healthy controls; thus only 6 out of top 25 OTUs differed at 4 months.

Figure 4B:
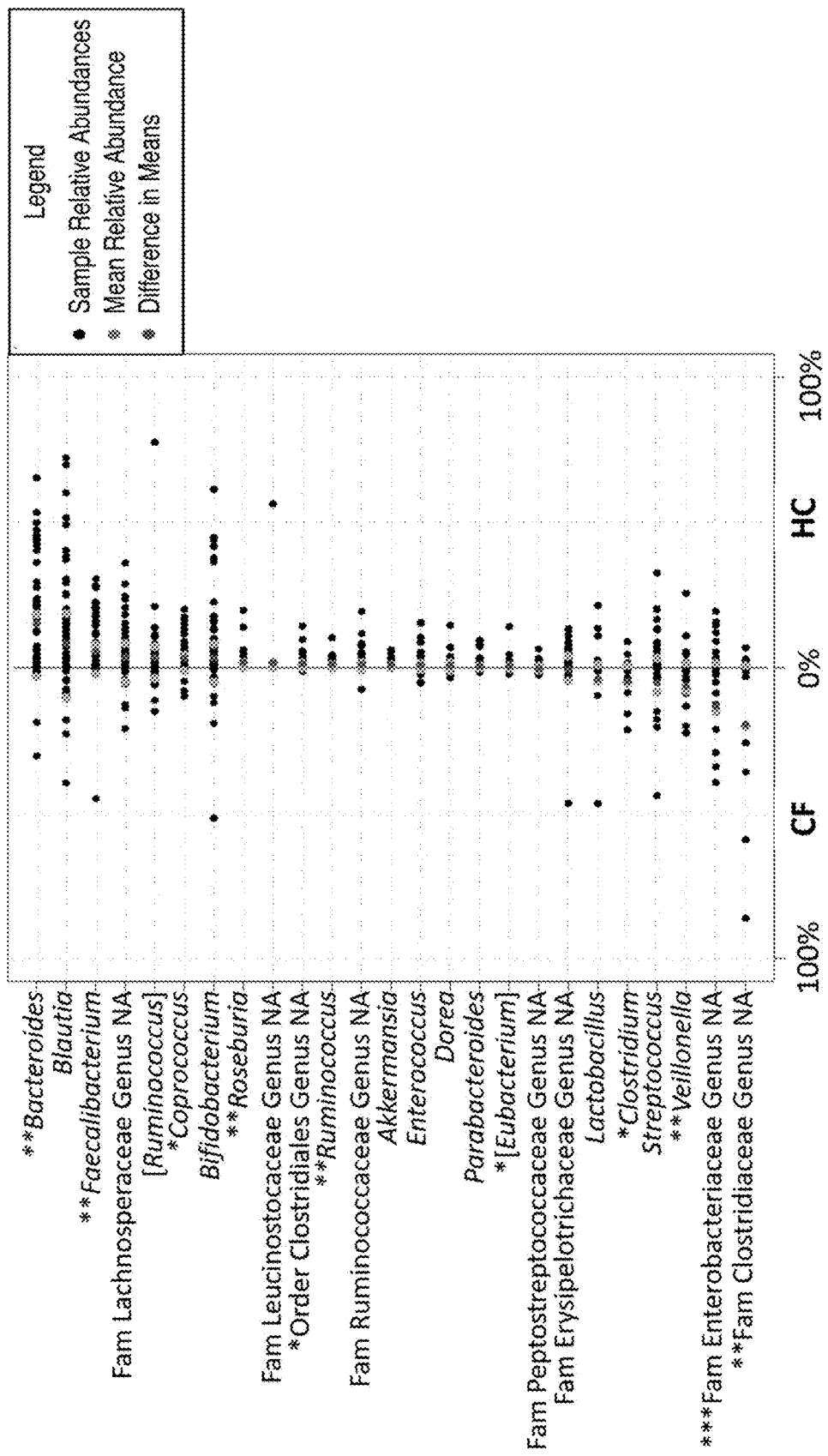

By one year of life, there were more significant differences between the cohorts, with 11 out of 25 OTUs showing a significant difference in relative abundance between these cohorts (FIG. 3B). For example, *Bacteroides* and *Faecalibacterium* were significantly higher in the healthy control group (FIG. 4B). There was no significant difference in Bifidobacteria levels between the cohorts at 1 year, despite the significant difference at 4 months. *Veillonella* and *Clostridium*, not but *Streptococcus*, were significantly higher in patients with CF at 1 year. These data support that, particularly early in life (i.e., at 4 months), the shift in microbes is primarily driven by a small subset of OTUs rather than a difference in the overall community of microbes present.

Example 1-4. Microbes Associated with Immune Programing are Lower in Patients with CF Compared to Healthy Controls Given that the data in FIGS. 4A and 4B indicate a reduction in *Bacteroides* and/or *Bifidobacterium* at 4 months and/or 1 year in patients with CF compared to the healthy controls, these two genera were further analyzed. While both groups have individual subjects with low levels of *Bacteroides* or *Bifidobacterium*, a comparison of the relative abundance of each microbe at each sampling time revealed that for the patients with CF at both 4 months and 1 year, there were a higher percentage of patients with <1% relative abundance of these microbes and a lower maximal relative abundance compared to the healthy cohort (FIGS. 5A and 5B).

Figure 5A:
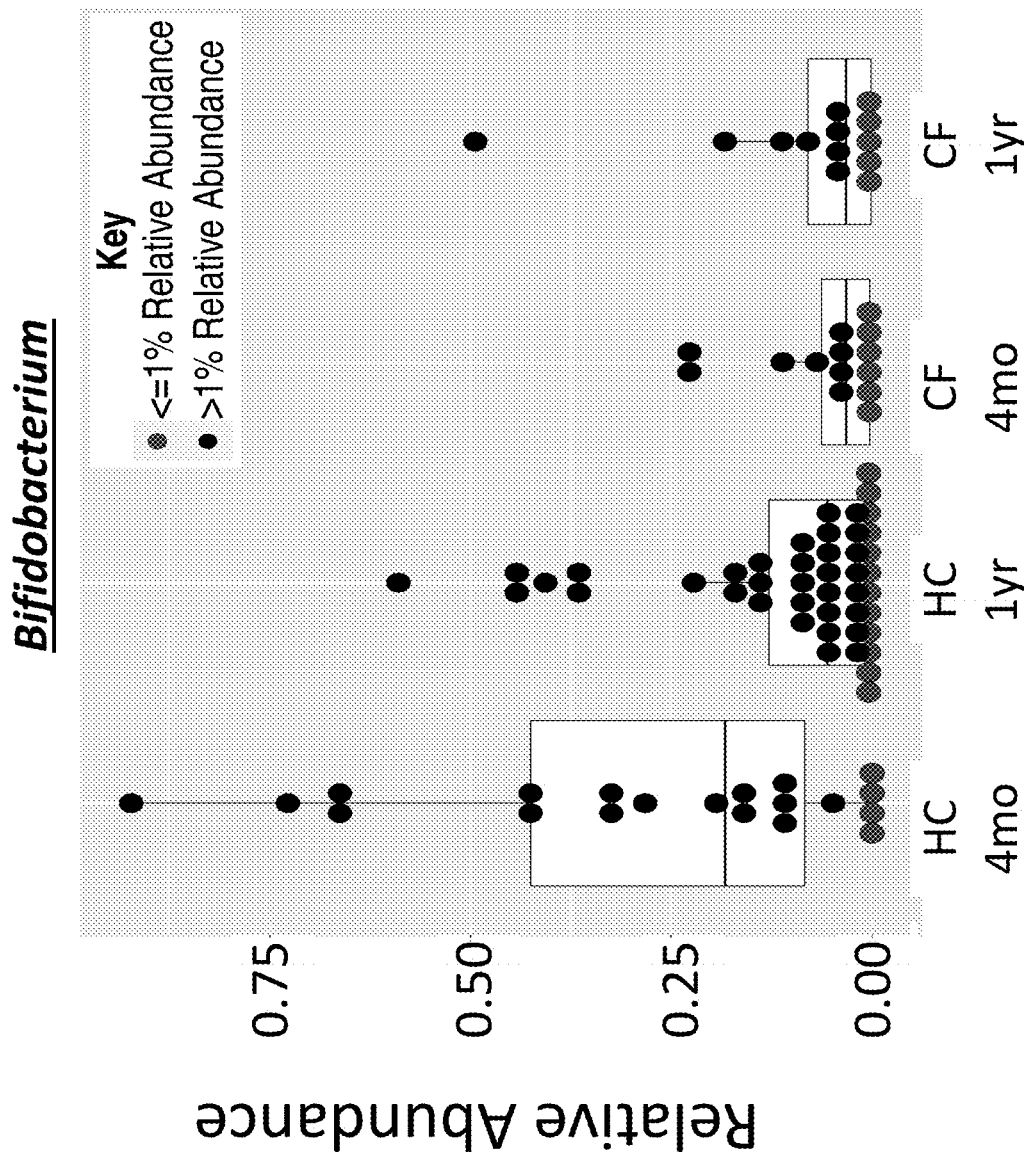
FIGS. 5A and 5B show range of relative abundance of *Bifidobacterium* and *Bacteroides* in the intestinal microbiome of samples from patients with CF and healthy controls. Each dot represents one subject with >1% relative abundance (black circle) and ≤1% relative abundance (red circle).
Figure 5B:
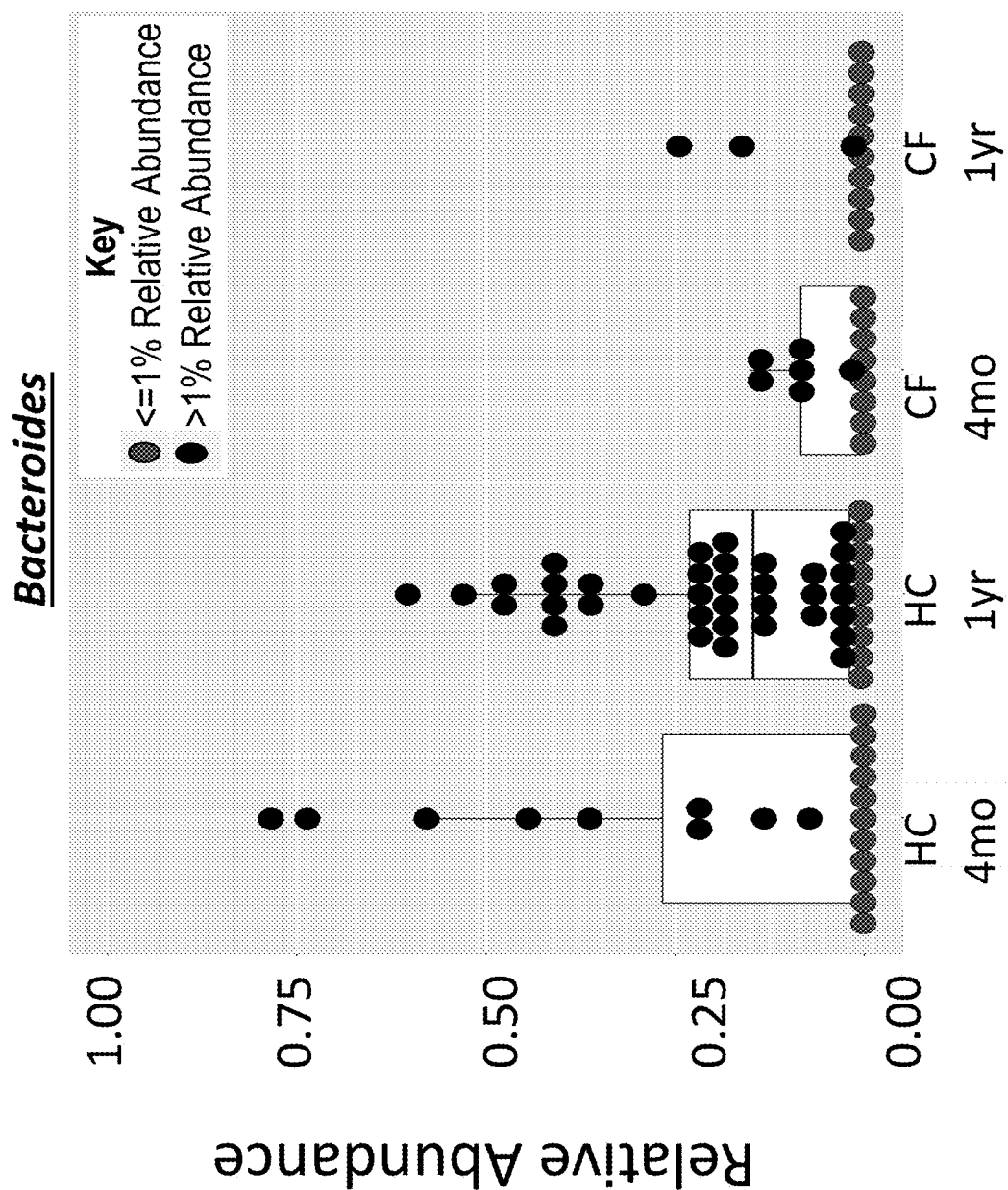
Figures 6A, 6B:
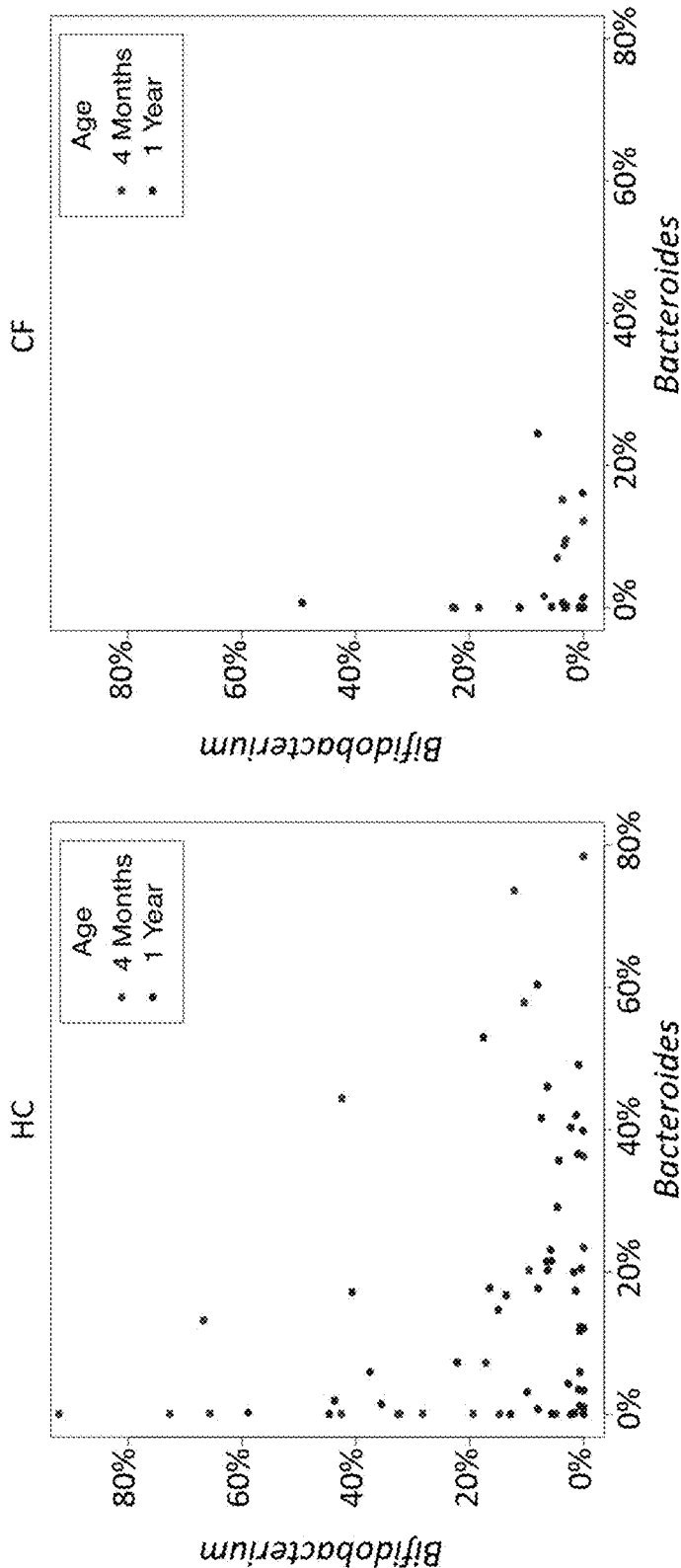
FIGS. 6A and 6B show subject-by-subject comparison of the relative abundance of *Bacteroides* and *Bifidobacterium*. Shown are scatter plots of the relative abundance of *Bifidobacterium* (y axis) versus *Bacteroides* (x axis) for the healthy controls (FIG. 6A) and patients with CF (FIG. 6B). Each dot represents one subject. The age of each subject is indicated by the color in the legend (4 months, green; 1 year, blue). The red box shows subjects with intermediate levels (~20-40%) of each genera.

Given the reported importance of *Bacteroides* and *Bifidobacterium* in immune programming (22, 23), it was a surprising result that even for the healthy controls, some individuals had <1% of these microbes (FIGS. 5A and 5B). To investigate this observation further, the relative abundance of *Bacteroides* and *Bifidobacterium* were plotted on a subject-by-subject basis for both groups (FIGS. 6A and 6B). For the healthy controls, many patients with low *Bacteroides* showed a high relative abundance of *Bifidobacterium*, and vice versa (FIG. 6A). There was also a group of healthy patients with an intermediate level of each microbe (FIG. 6A, red box) and ~50% of samples from the healthy controls had >40% relative abundance of *Bacteroides* and/or *Bifidobacterium*. In contrast, as shown in FIG. 6B, for the CF cohort, many of the subjects clustered in a group with <20% of each microbe, and there is only 1 subject with >40% of either *Bacteroides* or *Bifidobacterium* (~5% of the samples analyzed). These data support that the subjects with CF have lower levels of *Bacteroides* and *Bifidobacterium* even at 4 months of life.

Figure 7:
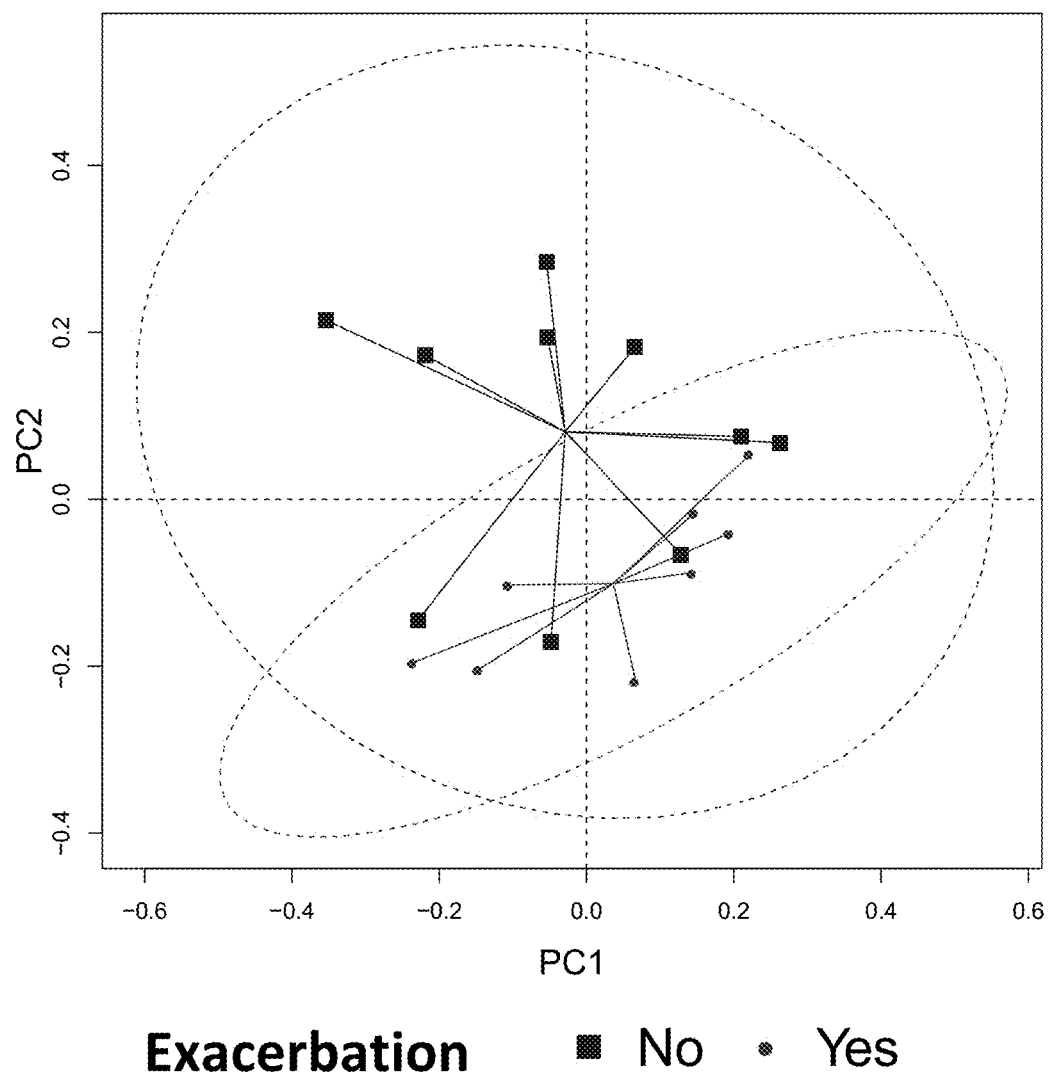
FIG. 7 shows PCoA plots generated from Generalized UniFrac distances between samples from patients with CF who have not had a pulmonary exacerbation (No, blue square) and samples from patients who have had a pulmonary exacerbation (Yes, green circle) at 1 year old (PERMANOVA p=0.09).
Figure 8:
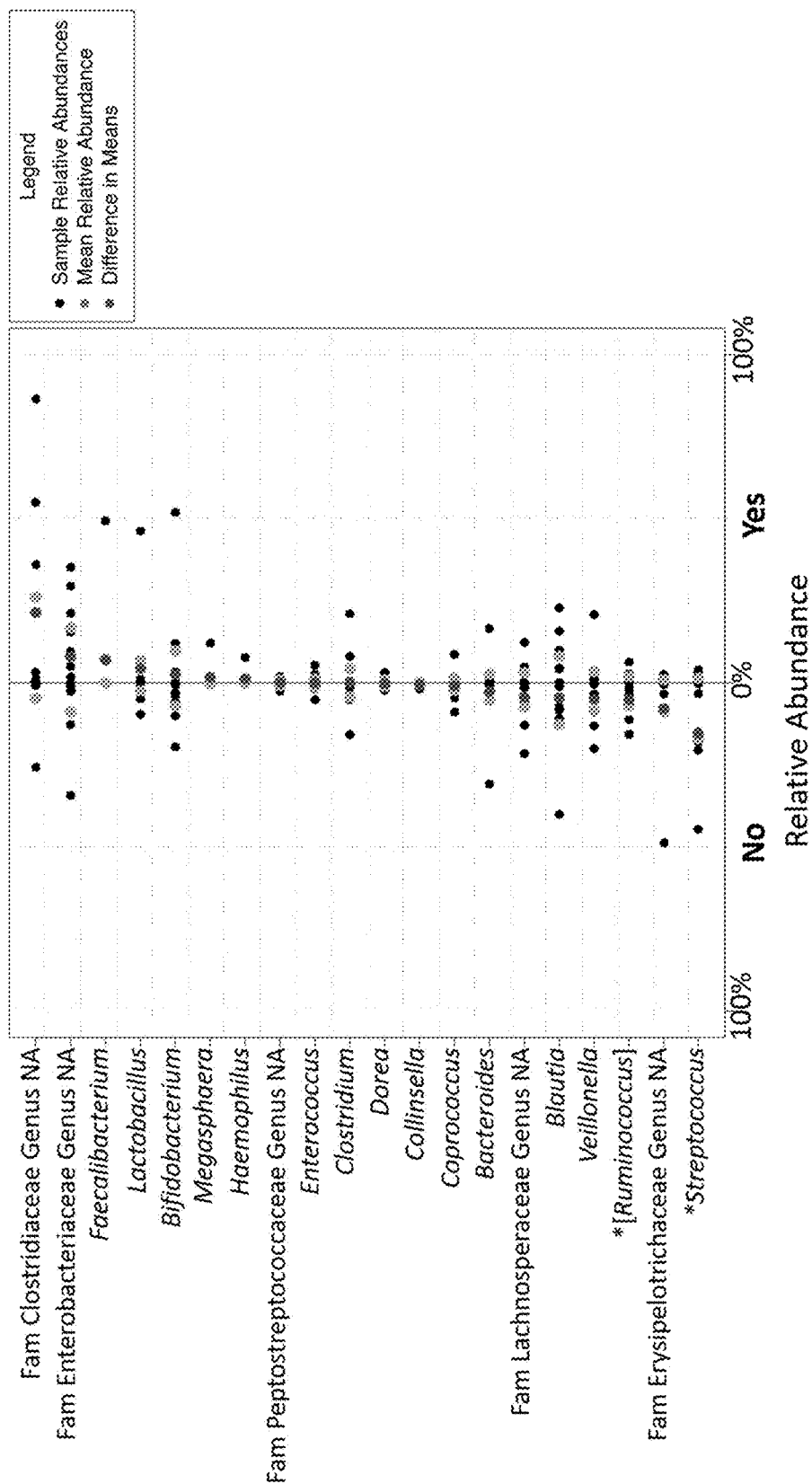
FIG. 8 shows comparison of relative abundance of top 20 OTUs present in samples from patients with CF at 12 months who have had a pulmonary exacerbation and those who have not had a pulmonary exacerbation. At 12 months, levels of *Streptococcus* and *Ruminococcus* were significantly higher in the stool samples of patients with CF who have not had a pulmonary exacerbation (No, left) versus those patients having a pulmonary exacerbation (Yes, right) after Bonferroni correction (*, p=0.022 (*Streptococcus*) and 0.035 (*Ruminococcus*)).

Example 1-5. Levels of *Streptococcus* Spp. are Significantly Higher in CF Patients Who do not Experience a Pulmonary Exacerbation in their First Year of Life Further, as shown in FIG. 7, the beta diversity of patients with CF was different from the beta diversity of healthy controls at 1 year of age (p=0.09, while p<0.05 at 6 months). This may show the two populations converged as they near 1 year of age. These same subjects had significantly different gastrointestinal community composition in relationship to risk of pulmonary exacerbation (p=0.03). Thus, a particular composition of microbiota in the intestine is associated with pulmonary exacerbation, a critical clinical event for patients with CF. Furthermore, as shown in FIG. 8, higher levels of *Streptococcus* in the intestinal community was significantly associated with protection from pulmonary exacerbations at 1 year of age (p=0.022 after Bonferroni correction). This association is significant after adjusting for antibiotic use in the period between pulmonary exacerbations and sampling. Similarly, there was a positive association between the levels of *Ruminococcus* and lack of pulmonary exacerbation in the first year (p=0.035 after Bonferroni correction; FIG. 8).

Figure 9:
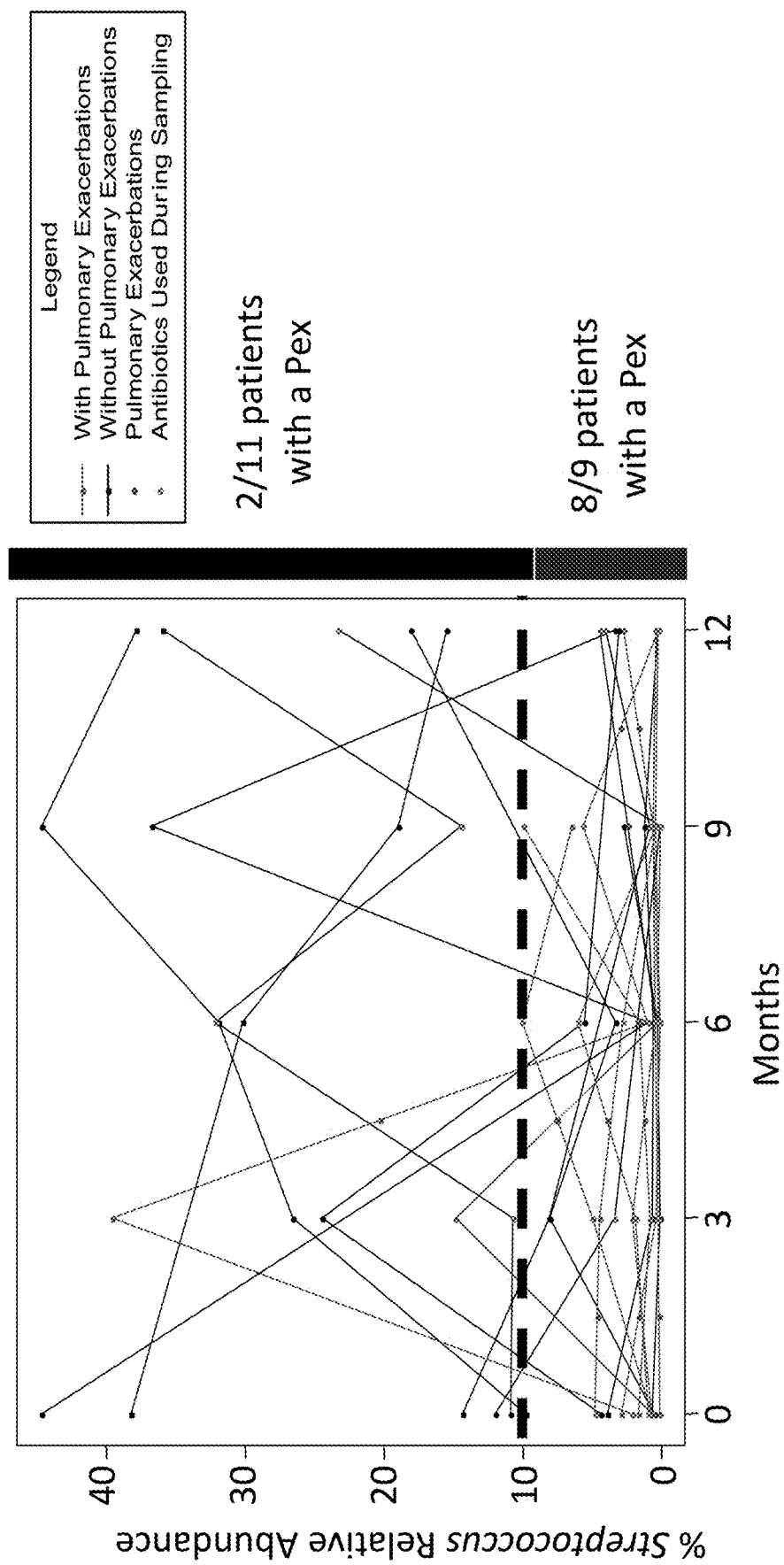
FIG. 9 shows changes in *Streptococcus* spp. relative abundance over time. The bars on the right indicate patients with lower than 10% *Streptococcus* in at least one sample time (red bar) or at least one sample of >40% *Streptococcus* (black bar). Dotted line indicates 10% relative abundance of *Streptococcus*, which is the median value for all samples. The numbers indicate the ratio of patients with exacerbations (numerator) and the number of patients in each group (denominator). The legend indicates patients with or without pulmonary exacerbations, with red dots indicating the time of the event and blue dots indicating the times of antibiotic treatment.

Samples from 20 subjects with CF were analyzed on a subject-by-subject basis, dividing them based on the relative abundance of *Streptococcus* (FIG. 9). For the subjects with CF that had <10% *Streptococcus* at two or more sampling times, 8 out of 9 subjects experienced pulmonary exacerbation in the first 12 months of life. In contrast, for those with >10% *Streptococcus* at one or more sampling times, only 2 out of 11 patients experienced an exacerbation. Higher levels of *Streptococcus* were significantly associated with the absence of pulmonary exacerbations in the first year of life (p=0.001).

Given the impact of presence of *Streptococcus* spp. in intestinal samples, a more detailed analysis was performed on the streptococcal species present in the samples from infants with CF. DNA extracted from a total of 15 samples was analyzed to identify the streptococcal species present in the samples based on the sequences previously identified (e.g., Mougeot et al., J Oral Microbiol, 2016; Belstrom et al., J Oral Microbiol., 2016; Gomes et al., J Endod., 2015). This analysis revealed that the primary streptococcal species present were *S. bovis*, *S. gallolyticus*, *S. macedonicus*, *S. alactolyticus*, *S. vestibularis*, *S. salivarius*, *S. mitis*, *S. parasanguinis*, *S. lutetiensis*, *S. equinus* and *S. infantarius*.

Example 1-6. Patients with CF and Healthy Controls Show Differential Enrichment of Predicted Metabolic Functions To examine if the changes in microbial abundance at 1 year are associated with differences in predicted metabolic function, PICRUSt analysis was used to assess the possible enrichment of metabolic functions in each of patients with CF and healthy controls.

A. PICRUSt Analysis

Open reference OTUs were removed from the OTU table using the QIIME function filter_otus_from_otu_table for use with Phylogenetic Investigation of Communities by Reconstruction of Unobserved States (PICRUSt), as previously reported (e.g., Langille et al., Nat Biotechnol, 2013). The OTU table was then normalized by copy number, then functional predictions are assigned by PICRUSt from the KEGG Ortholog database. KEGG Orthologs are then collapsed into KEGG Pathways using the categorize by function PICRUSt script. The resulting file was then imported into R for the analysis of pathway abundance predictions between patients with CF and healthy controls. Any pathways that were found to be significantly different after FDR multiple testing correction between patients with CF and healthy controls using the Wilcoxon rank-sum test were then manually filtered to include only bacterial pathway predictions.

Figure 10:
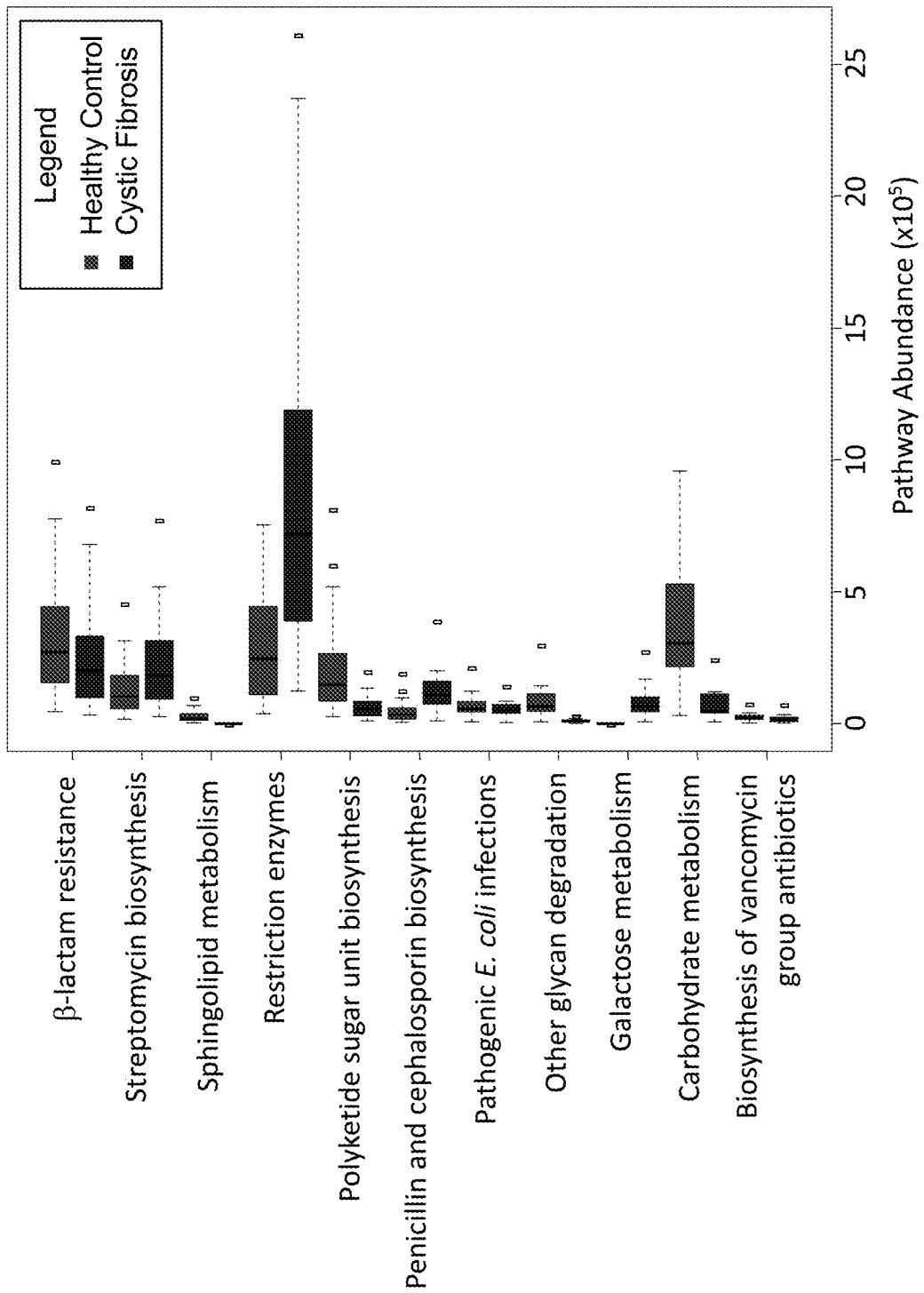
FIG. 10 shows analysis of intestinal microbiota for enrichment of predicted metabolic functions between samples from patients with CF and healthy controls at 1 year of age. Pathways and respective abundance levels were generated from PICRUSt metagenome predictions with FDR multiple testing correction as described in Example 1-2.

Relative to the healthy controls, the subjects with CF at 1 year was associated with a decrease in functions associated with a variety of processes, including β-lactam resistance, polyketide sugar unit biosynthesis, and carbohydrate metabolism (FIG. 10). In contrast, the subjects with CF showed enrichment in processes that include restriction enzymes, streptomycin biosynthesis, penicillin and cephalosporin biosynthesis, and galactose metabolism (FIG. 10). The analysis of 4 months samples showed no significant enrichment of pathways for either cohort, despite the significant differences in abundance of several OTUs, as shown in FIGS. 4A and 4B.

Example 1-7. Apical Application of *Bacteroides* to Intestinal Epithelial Cells Reduces Basolateral Release of IL-8

Next, the mechanism by which change in intestinal microbiota impacts airway exacerbation was studied. Systemic levels of inflammation or immune response likely contributes to airway exacerbation. Specifically, the impact of apical application of *Bacteroides* spp. on the basolateral production of IL-8 was studied.

A. Tissue Culture Experiments

Figure 11:
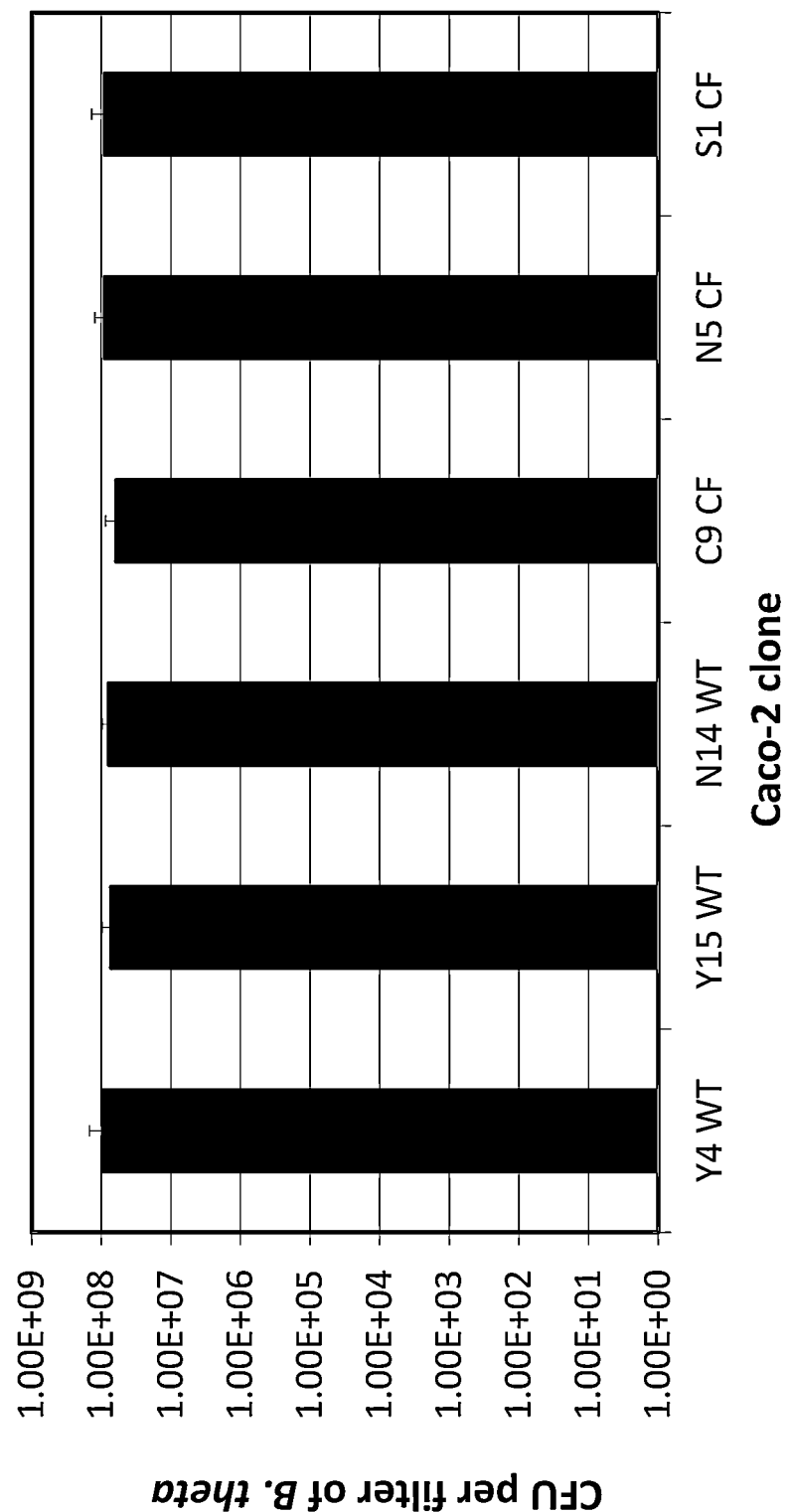
FIG. 11A shows colonization of three different wild type Caco-2 cell lines and three different ΔCFTR/ΔCFTR Caco-2 lines by *Bacteroides thetaiotaomicron* (abbreviated *B. theta*).
FIG. 11B shows the relative levels of IL-8 production at basolateral and apical faces of filter-grown, polarized monolayers of Caco-2 cells in the presence and absence of *B. theta*.

Three different WT lines (Y4, Y15, N14) and three different ΔCFTR/ΔCFTR Caco-2 cell lines (C9, N5, S1) were cultured (See FIG. 11A). Cells were grown on transwell filters for ~1 week to allow confluent growth of airway cells on the filters, enabling collection of the IL-8 produced from the apical and basolateral faces of the monolayer. *Bacteroides thetaiotaomicron* (*B. theta*) ($1.3 \times 10^8$ cells of VPI 5482) was applied to the apical face of the monolayer on the filter, while the basolateral compartment was not exposed to this bacterium. Filters were incubated anaerobically for 3 hours and then the added suspension of bacteria was removed and replaced with fresh medium. Filters were returned to anaerobic incubation overnight. To determine CFU, filters were scraped and plated (n=3 for each cell clone). ELISA assay (PromoKine) was performed to measure IL-8 levels.

Figure 11B:
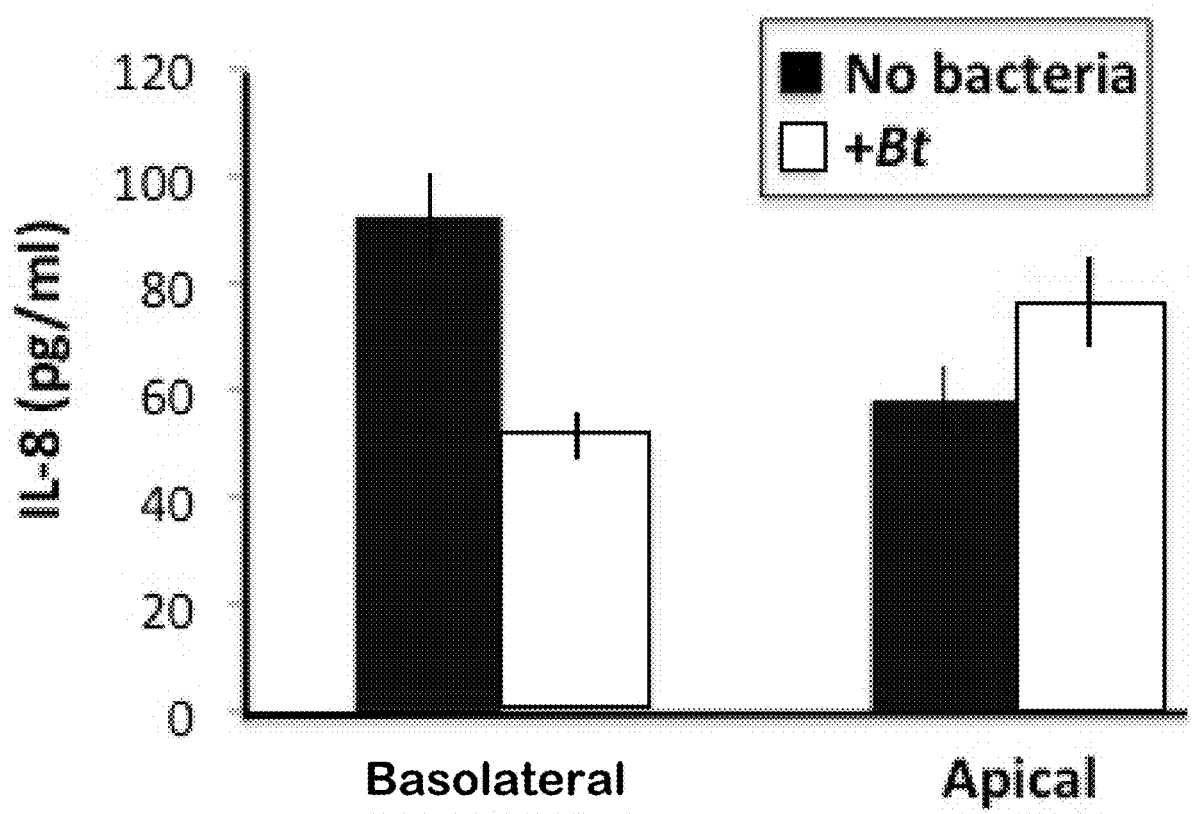

The ability of *B. theta* to colonize three different wild type and CFTR-defective Caco-2 cell lines were assessed. Equal colonization of all three lines by *B. theta* were observed (FIG. 11A). Next, *B. theta* was exposed to one of the wild type Caco-2 cell lines. Apical exposure of the WT cell line to *B. theta* resulted in reduced basolateral production of IL-8, and a small increase in the apical production of this cytokine (FIG. 11B). These data support that changes in the intestinal lumen could have systemic effects on inflammation that could lead to pulmonary exacerbation.

These findings show that patients with CF, as early as 4 months of life, show a depletion in key immune modulatory microbes. It has previously been noted that *Bacteroides* and *Bifidobacterium* in patients with CF are decreased in the intestine prior to their first pulmonary exacerbation, although this trend was not significant after multiple testing correction. The loss of *Bacteroides* and Bifidobacteria does not appear to have a cascading effect on the rest of the intestinal microflora, indicating that the underlying defect in the intestinal environment in young patients with CF results in a focused difference from early life primarily manifested by missing microbes in the composition of the intestinal microflora. By one year of age, while the alpha diversity of the communities for the CF and healthy cohort are not significantly different, 11/25 OTUs show a significant difference in relative abundance between these cohorts, indicating that the communities continue to diverge. This divergence is reflected by the significant difference in several metabolic pathways at one year as assessed by the PICRUSt analysis. Furthermore, while enzyme replacement therapy has clearly had positive, transformative impacts on patients with CF (6, 28, 29), the differences observed and reported herein in the stool microbiota of the CF cohort indicate that these patients still have underlying defects and suggest room for improvement in such therapeutic interventions.

The studies reported herein show that higher levels of *Streptococcus* spp. in the stools of patients in the CF cohort are associated with a significantly lower frequency of pulmonary exacerbation. The reduction in *Bacteroides* and *Bifidobacterium* compared to healthy controls shown here are likely leaving an ecological niche unoccupied in patients with CF. It is possible that diverse *Streptococcus* species in the intestine of children with CF act to fill the role of mediating host immunity that *Bifidobacterium* and *Bacteroides* perform in healthy children. Alternatively, colonization by *Streptococcus* species may prevent the colonization of other microbes by the process of niche exclusion. While additional mechanistic studies are required to establish such a relationship, these findings raise that possibility that probiotic interventions early in life may help drive the developing intestinal flora to a more health-promoting state.

The data provided herein show that *Bacteroides* added to the apical face of the airway cells (e.g., the part of the cell facing into the intestinal lumen) reduced the production of IL-8 from the basolateral face of the cell (which can direct this cytokine systemically.) These data indicate a possible mechanism whereby intestinal bacteria can impact systemic immunity and disease progression.

Example 2-1. The Intestinal Microbial Communities of Infants with CF and Healthy Controls Over the First Year of Life A. Patient Population Institutional review board approval was obtained from the Center for the Protection of Human Subjects at Dartmouth College with yearly renewal of the approval. Eligibility criteria for the CF cohort included: diagnosis with CF prenatally or postnatally based upon newborn screening results and subsequent confirmation with sweat chloride and genetic testing. Subjects were eligible if their care for CF would be at the Dartmouth-Hitchcock Medical Center in Lebanon, NH or Manchester, NH affiliated clinics. Subjects were excluded if they had non-CF chromosomal anomalies. For the comparison control group without CF, infants were selected from the New Hampshire Birth Cohort Study (NHBCS) if they were delivered at term gestation and provided at least 2 stool samples during their first year of life. For the NHBCS, pregnant women ages 18-45 were recruited from prenatal clinics as described: women were screened for eligibility at an initial prenatal care visit and were enrolled at 24-28 weeks' gestation if they reported using water from a private, unregulated well in their home since their last menstrual period and were not planning a change in residence prior to delivery. Only singleton, live births were included in the cohort.

Samples from 21 infants with CF and 409 general population controls (Table 1) were analyzed. The control subjects were selected from a cohort recruited for the New Hampshire Birth Cohort Study from whom at least 2 stool samples were collected during the first year of life at 6 weeks, 4 months, 6 months, 9 months, and/or one year of age.

TABLE 1

Summary of the subjects analyzed at each time point.

| Age[a] | Number of Samples | Feeding Mode | | | Pancreatic Insufficient (%) | Delivery Mode (% Vaginal) |
|---|---|---|---|---|---|---|
| | | BF[b] | Formula | Mixed | | |
| Cystic Fibrosis | | | | | | |
| 6 Weeks | 18 | 11% | 44% | 44% | 83% | 44% |
| 4 Months | 12 | 8% | 42% | 44% | 83% | 67% |
| 6 Months | 15 | 7% | 47% | 47% | 80% | 53% |
| 9 Months | 14 | 14% | 57% | 29% | 79% | 50% |
| 12 Months | 17 | 12% | 47% | 41% | 82% | 53% |
| Total | 76 | 11% | 47% | 42% | 81% | 53% |
| Control Population | | | | | | |
| 6 Weeks | 391 | 77% | 4% | 19% | NA | 72% |
| 4 Months | 30 | 77% | 0% | 23% | NA | 93% |
| 6 Months | 28 | 61% | 0% | 39% | NA | 93% |
| 9 Months | 30 | 47% | 0% | 53% | NA | 93% |
| 12 Months | 323 | 30% | 4% | 67% | NA | 71% |
| Total | 802 | 56% | 3% | 40% | NA | 74% |

[a]Each time point listed represents a range of samples around that time point as follows: 6 weeks (2-14 weeks), 4 months (3-5 months), 6 months (5-8 months), 9 months (8-11 months), and 12 months (11-16 months).
[b]"BF" indicates breast fed. All percentages were rounded to the nearest whole percent.

B. Analysis of Microbial Populations in Stool

Stool samples were collected and processed as described above. DNA was extracted from stool samples and analyzed for microbial communities via sequencing of the 16S rRNA.

The 16S rRNA gene sequence reads for subjects with CF and controls were demultiplexed and stored in paired-end forward and reverse read fastq files. Primer sequences were then removed, and all subsequent analyses were performed in R version 3.5.1. All samples were processed through the DADA2 (v1.10.0, 47) pipeline for quality filtering and trimming, dereplication, and merging of paired end reads. An amplicon sequence variant (ASV) table was constructed and chimeras were removed. Taxonomy was assigned from the SILVA database. The final mean read count in CF patients was 116,993.8 (+/−50,311.98 SD) and 109,920 (+/−62,345.95 SD) in controls.

C. Statistical Analyses

Within sample alpha-diversity was determined using the Shannon diversity index as calculated for each sample in the phyloseq (v1.26.0, 49) R package function estimate_richness. Significant differences in alpha diversity were determined using Wilcoxon rank-sum with FDR correction for multiple testing and subsequently verified with linear regression controlling for age, pancreatic insufficiency, feeding mode, delivery mode, pulmonary exacerbations and antibiotics use prior to the particular sampling period. For the purposes of this study, antibiotic use prior to sampling is defined as any oral or intravenous antibiotics administered at any time from birth to the time of sample collection. Delivery mode was included in all models that adjusted for antibiotics use to control for confounding, as women who delivered by cesarean section are treated with antibiotics prior to surgery per clinical protocol. The final alpha diversity model selected controlled for age, feeding mode, and delivery mode as all other covariates were not found to have a significant effect on alpha diversity. Since Shannon diversity index can be influenced by read depth, fisher's alpha and Shannon diversity index were calculated after rarefaction. Consistent patterns across all alpha diversity methods were observed. Differences in the microbial profiles of stool samples from 21 subjects with CF and 409 comparison infants were analyzed using Generalized UniFrac Distances from the GUniFrac R package (v1.1, 50) calculated from a midpoint-rooted phylogenetic tree generated by phangorn (v2.4.0, 51). Distances were visualized using principal coordinate analysis (PCoA) plots and the significance of clustering was determined through permutational multivariate analysis of variance (PERMANOVA) from vegan (v2.5-3, 52). These results were confirmed using Bray-Curtis distances, which were consistent with the patterns observed using Generalized UniFrac distances. Significant differences in the relative abundance of individual taxa were determined with a Wilcoxon rank-sum test with FDR correction to adjust for multiple testing and verified with linear models adjusting for age, feeding mode, antibiotics prior to sampling, delivery mode, pancreatic insufficiency, and pulmonary exacerbations.

Figure 12:
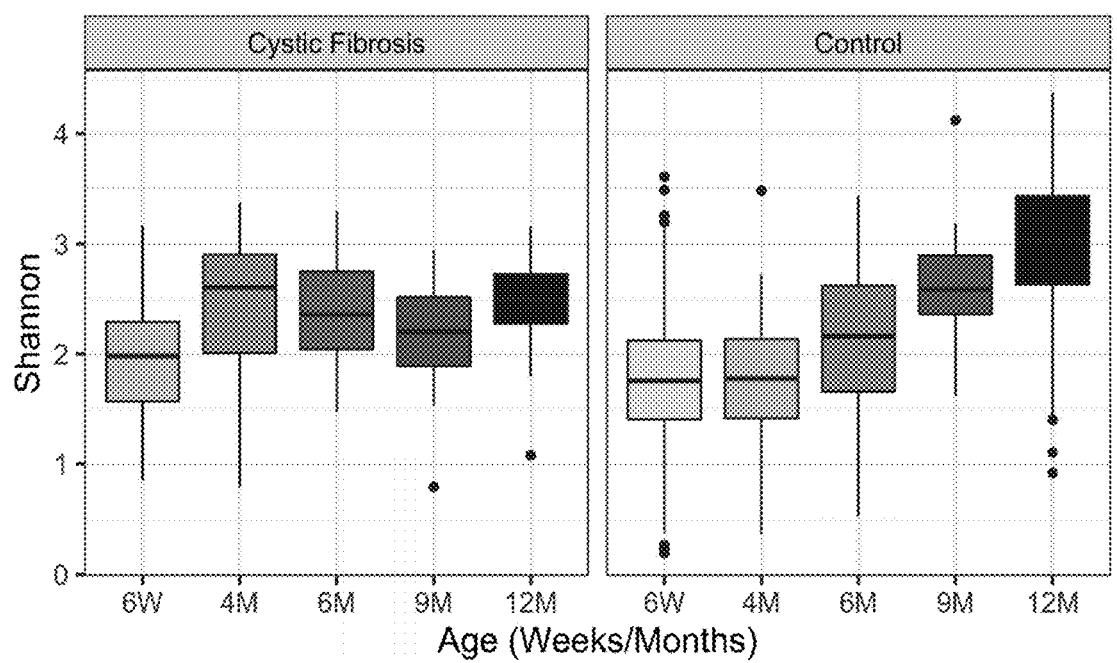
FIG. 12 shows a comparison of the alpha diversity between subjects with CF and infants without CF. Shown is the Shannon alpha diversity measures for the healthy cohort (Control, right) versus cohort of children with CF (CF, left) at the indicated times over the first year of life. The boxes span the first and third quartile of the data with the median value indicated as the central horizontal black line. Outliers are indicated as points beyond the span of the whiskers. The Wilcoxon rank-sum was used for all comparisons and FDR correction was applied for multiple testing correction

D. The Alpha Diversity of Stool Communities is Altered in Infants with CF in the First Year of Life To examine the impact of CF on community (alpha) diversity, the Shannon Diversity Index (SDI) for infants with and without CF were analyzed at 6 weeks, 4 months, 6 months, 9 months, and one year of age. The alpha diversity of infants with CF did not follow the expected and previously reported pattern of increased diversity over the first year of life observed for the control cohort (FIG. 12). While the difference in alpha diversity between the two cohorts did not reach significance at 6 weeks of age (p=0.18) infants with CF had higher alpha diversity at 4 months (p=0.016), but were surpassed by the control infants by 9 months of age (p=0.014). By 12 months of age, infants in the control cohort had significantly higher alpha diversity than infants with CF of the same age (p<0.001). Within the CF cohort there was only a modest increase in diversity from 6 weeks to 12 months that was not significant after false discovery rate (FDR) correction (p=0.06955). This small change in diversity of microbes in the stool for the CF population over the first year of life is in stark contrast to the significant increase observed in the control cohort (p<0.0001). These data indicate a significant difference in the community diversity associated with the stool of infants with CF versus the comparison group of control infants as early as 4 months of age.

Figure 13:
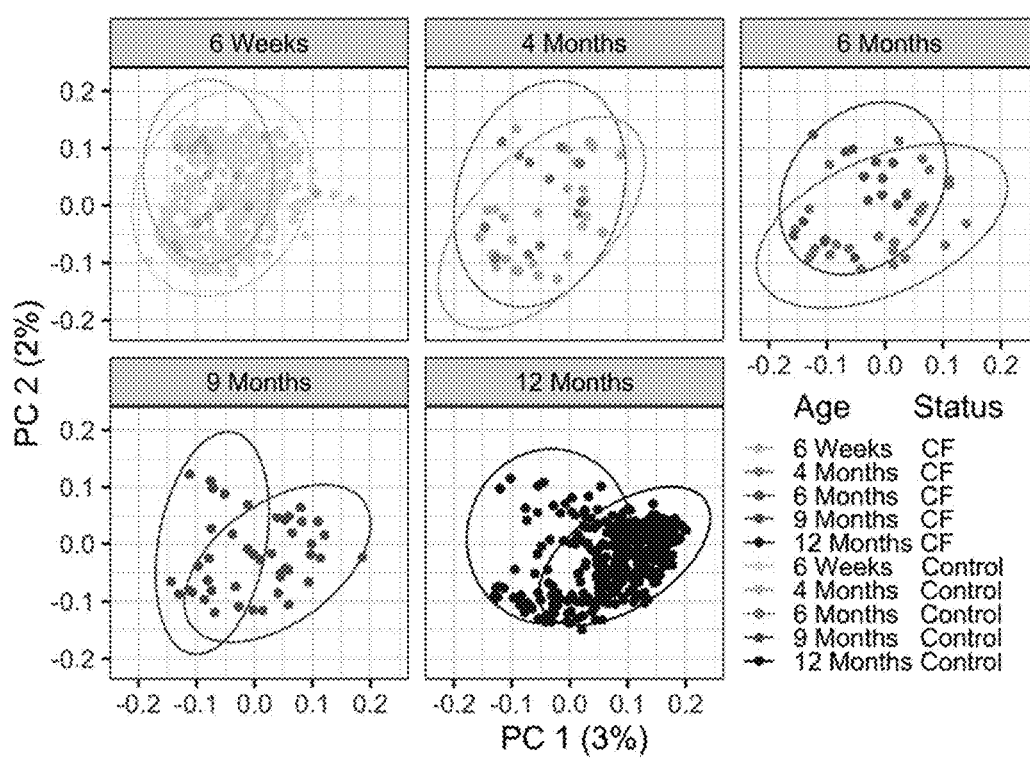
FIG. 13 shows a comparison of the beta diversity of CF and control cohorts over time. The beta diversity of CF samples (CF), as measured by generalized UniFrac distances, is significantly different from that of healthy controls (HC) at all time points. Each dot represents a unique sample, and the age and source of the samples is indicated by the color of the dot depicted in the legend. By PERMANOVA, p=0.015 at 6 weeks, p=0.004 at 4 months, and p=0.001 at the remaining time points of 6, 9, and 12 months of age.

The beta diversity (microbial community composition) of the infants with CF were analyzed in comparison to the control infant group. The beta diversity of subjects with CF and controls is significantly different across all 5 time points (FIG. 13; PERMANOVA of generalized UniFrac distances; p=0.001), consistent with the difference in alpha diversity for controls over time in the first year of life. For infants with CF, the similar alpha diversity across the first year is also reflected by the clustering of communities, with no significant difference in beta diversity across time in the CF cohort (PERMANOVA of generalized UniFrac distances; p=0.397).

Example 2-2. Clinical Covariates Associated with Stool Microbiota of Infants with CF and Controls: Beta Diversity is Associated with Airway Exacerbation While feeding mode is significantly associated with beta diversity in control infants (PERMANOVA p=0.001), this effect did not reach significance among the subjects with CF (PERMANOVA p=0.081). Similarly, delivery mode has previously been shown to significantly affect the gut microbiota of infants in the New Hampshire Birth Cohort Study (23) but this effect was not observed in the CF cohort (PERMANOVA p=0.287). Additionally, pancreatic insufficiency is a significant factor in the gut microbial composition of infants with CF (PERMANOVA p=0.034) but pancreatic insufficiency did not account for the differences observed between infants with CF and controls. That is, when restricting the analysis to only pancreatic sufficient subjects there remained a significant difference between pancreatic sufficient subjects with CF and controls without CF across all time points (PERMANOVA p=0.002).

Figure 14:
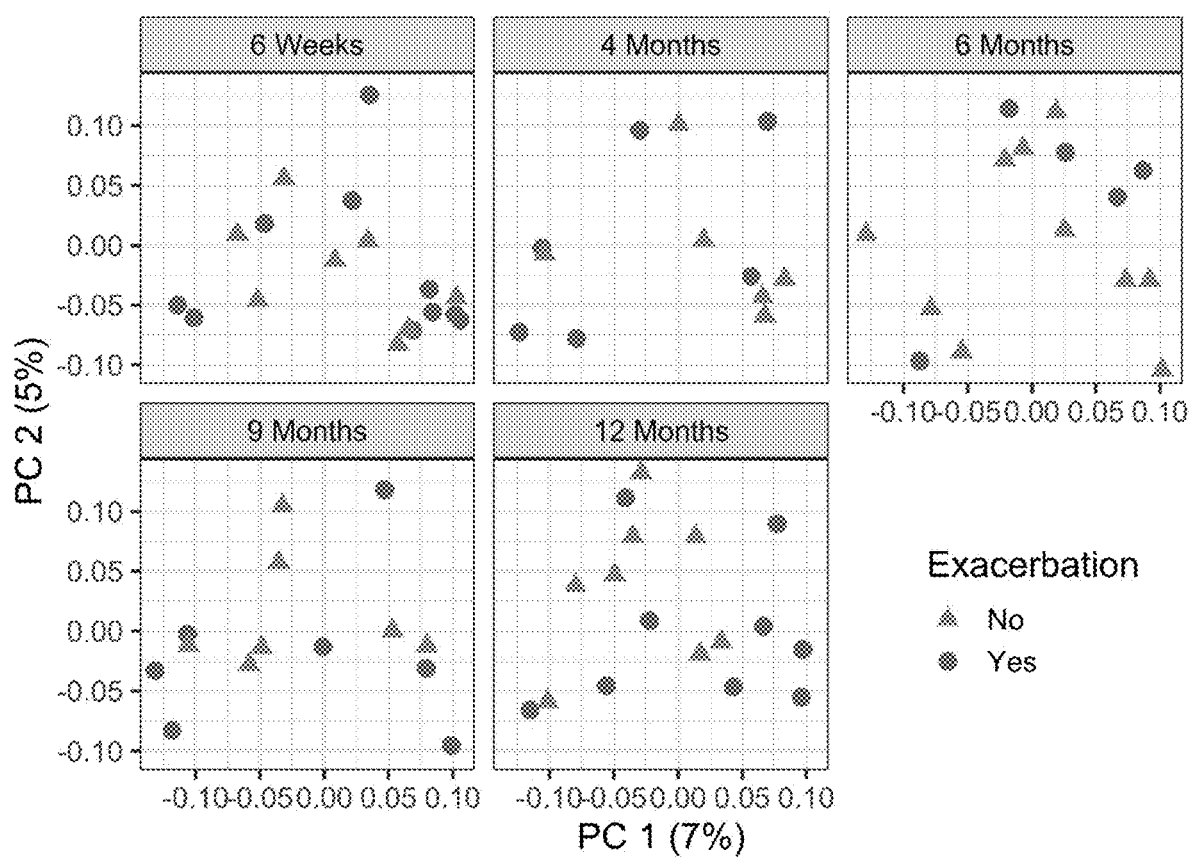
FIG. 14 shows a beta diversity plot for CF patients having an airway exacerbation event (circles) and CF patients having no such event (triangles). Beta diversity is associated with airway exacerbation in infants with CF. These principal coordinates analysis (PCoA) plots depict samples from CF patients at all 5 time points: 6 weeks, 4 months, 6 months, 9 months, and 12 months of age. As indicated in the legend, purple circles denote that this subject had an exacerbation event in the first year of life, while blue triangles indicate no such event in the first year. Adjusting for age to account for repeated measures, pulmonary exacerbations in the first year of life were significantly associated with beta diversity, as measured by generalized UniFrac distances (PERMANOVA p=0.041).

Finally, given the observed association between beta diversity of the stool microbiota and airway exacerbation in CF subjects in a previous study of 13 subjects (0-34 months) (16), that same question was examined here with this larger cohort. A significant association between beta diversity and airway exacerbation in this CF cohort was observed (FIG. 14). These data reinforce the conclusion that there is a link between stool microbial composition and airway disease.

Figure 15:
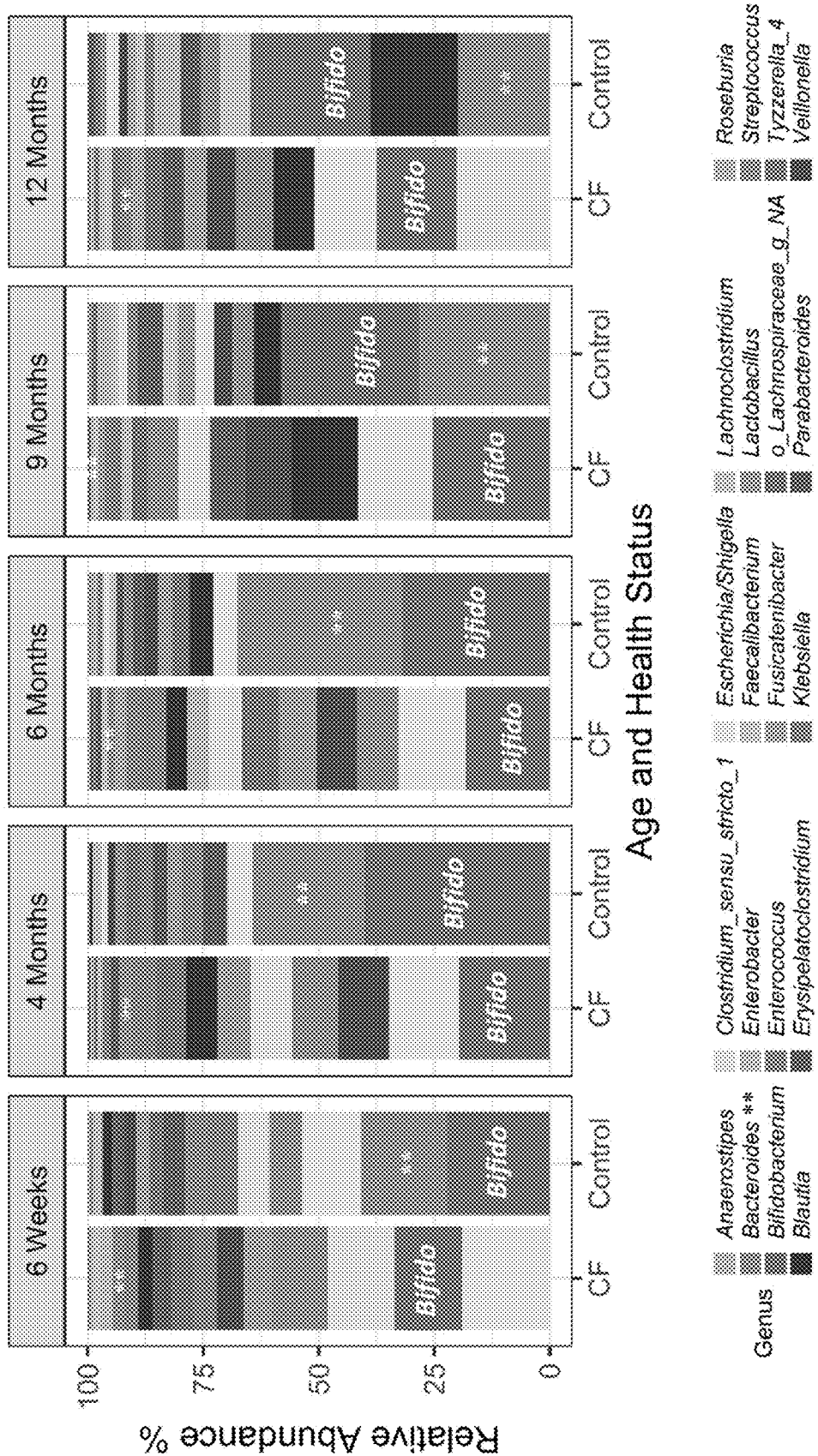
FIG. 15 shows a comparison of relative abundances of genera for subjects with CF and the control group over the first year of life. Relative abundance of the top 20 taxa present in stool samples. Abbreviations: NA, not assigned. The legend at the bottom corresponds to the colors in the stacked bars.

Example 2-3. Microbes Associated with Immune Programing are Decreased in Infants with CF Compared to Controls Given the differences in community composition measures between CF and control cohorts (i.e., alpha and beta diversity) in the first year of life, the relative abundance of the top twenty taxa over the first year of life was examined (FIG. 15). These top 20 taxa account for 85% and 88% of the diversity in the CF and control cohorts, respectively.

Figure 16:
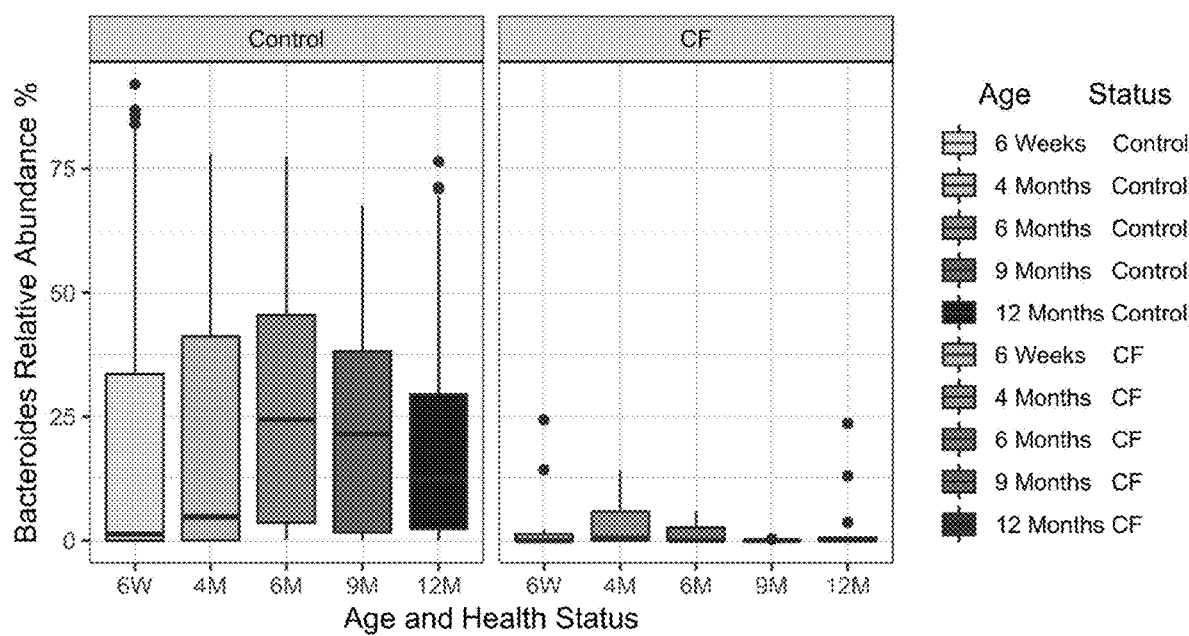
FIG. 16 shows relative abundance of *Bacteroides* in CF and healthy infants over the first year of life. Infants with CF have significantly lower levels of *Bacteroides* in their stool across all time points in their first year of life Wilcoxon rank-sum p<0.001. The time points assessed are indicated, and the bars are color coded by time, as indicated in the legend. The boxes span the first and third quartile of the data with the median value indicated in black. Outliers are indicated as points beyond the span of the whiskers.

Interestingly, a major shift in the microbiota between the two cohorts was not observed in aggregate or at any particular time point, with the greatest differences observed at 12 months. Indeed, while a significant depletion of *Bacteroides* spp. was observed (average of 1.9% in CF vs. 19% in control across all samples) across all time points even after correcting for the false discovery rate (FIG. 16), in aggregate over the first year of life the only other taxa significantly different between these populations were *Roseburia* (0.05% in CF and 0.9% in control) and *Veillonella* (8% in CF and 2.3% in control). A few other selected microbes were significantly depleted at individual time points, but they were not consistently different over the first year of life.

*Bacteroides* and *Bifidobacterium* have been reported to play an important role in immune programming, thus it was unexpected that even for the controls, some individuals had <1% of these genera. To investigate this observation further, the relative abundance of *Bacteroides* versus *Bifidobacterium*, this second known immune modulating microbe, was examined on a subject-by-subject basis for both cohorts. For the control cohort, many subjects with low *Bacteroides* showed a high relative abundance of *Bifidobacterium*, and vice versa. There was also a group of control subjects with an intermediate level of each microbe. In contrast, for most subjects in the CF cohort the low abundance of *Bacteroides* spp. is notable, and only ~20% of the samples showed a relative abundance of *Bifidobacterium* above 50%. Thus, many subjects with CF demonstrated relatively low levels of both immune-modulating microbes.

Example 2-4. Apical Application of *Bacteroides* to Intestinal Epithelial Cells Reduces Production of IL-8

The data demonstrates that *Bacteroides* spp. are significantly reduced in the intestinal microbiota of infants with CF at every time point assessed. Depletion of this immune-modulating microbe is one of the key changes that drive the observed differences in the alpha and beta diversity between the CF and control cohorts. These observations raise the question of how changes in *Bacteroides* spp. levels in the intestine might impact the physiology of the airways.

A recent report examining the impact of *Bacteroides* in intestinal epithelial cells provides a clue to the role of *Bacteroides* in reducing systemic inflammation. Some *B. fragilis* strains produce enterotoxins that can stimulate the production of IL-8. Cho and colleagues showed that exposing the apical face of intestinal epithelial cells to such a toxin resulted in the increased production of IL-8 from the basolateral face of the same cell monolayer. These data indicate that impacts to the host cells in the lumen of the intestine may have systemic impacts on cytokine production. Thus, the impact of apical application of *Bacteroides* spp. on the production of IL-8 from the apical and/or basolateral face of these cells was assessed.

To investigate this mechanism, an experiment was performed whereby Caco-2 cells were grown on transwell filters as polarized monolayers for ~4 weeks. Two different Caco-2 cell lines were used—one line carried loss of function mutation in the CFTR gene generated via Cas/CRISPR (ΔCFTR) and the other line was WT for CFTR, but was subject to the same mock manipulations used to generate the ΔCFTR line. The basal level of IL-8 produced by both cell lines was low (~90 pg/ml of IL-8 on the apical face, —20 pg/mL on the basolateral face). Stimulation of the cell lines with 100 ng/ml of TNFα for 24 hours resulted in a marked increase in IL-8 production for both cell lines, and furthermore significantly more (~2-5-fold) IL-8 production for the ΔCFTR line compared to the WT control (student t-test, P<0.05) was observed. Thus, in all subsequent experiments TNFα was added to stimulate IL-8 production.

Apical application of *Bacteroides* to the TNFα-treated cells lines resulted in a reduction in IL-8 levels. To this end, ~3.5×10$^7$ CFU *Bacteroides thetaiotaomicron* VPI (*B. theta* VPI) was applied to the apical face of the TNFα-treated ΔCFTR and WT intestinal cell lines. *B. theta* VPI was not introduced into the basolateral compartment.

The filters were incubated anaerobically for 3 hours after treatment, and then the added suspension of bacteria was removed and replaced with fresh medium. Filters were returned to anaerobic incubation overnight. Twenty four hours after initial application of the bacteria, supernatants were collected and IL-8 levels measured via ELISA assay (PromoKine or Biolegend). To determine CFU, filters were scraped and plated (n=6); at the end of the experiment there were ~2×10$^9$±4×10$^8$ CFU bacteria/well associated with the apical face of both monolayers, with no significant difference between the cells colonizing each monolayer.

Figure 17:
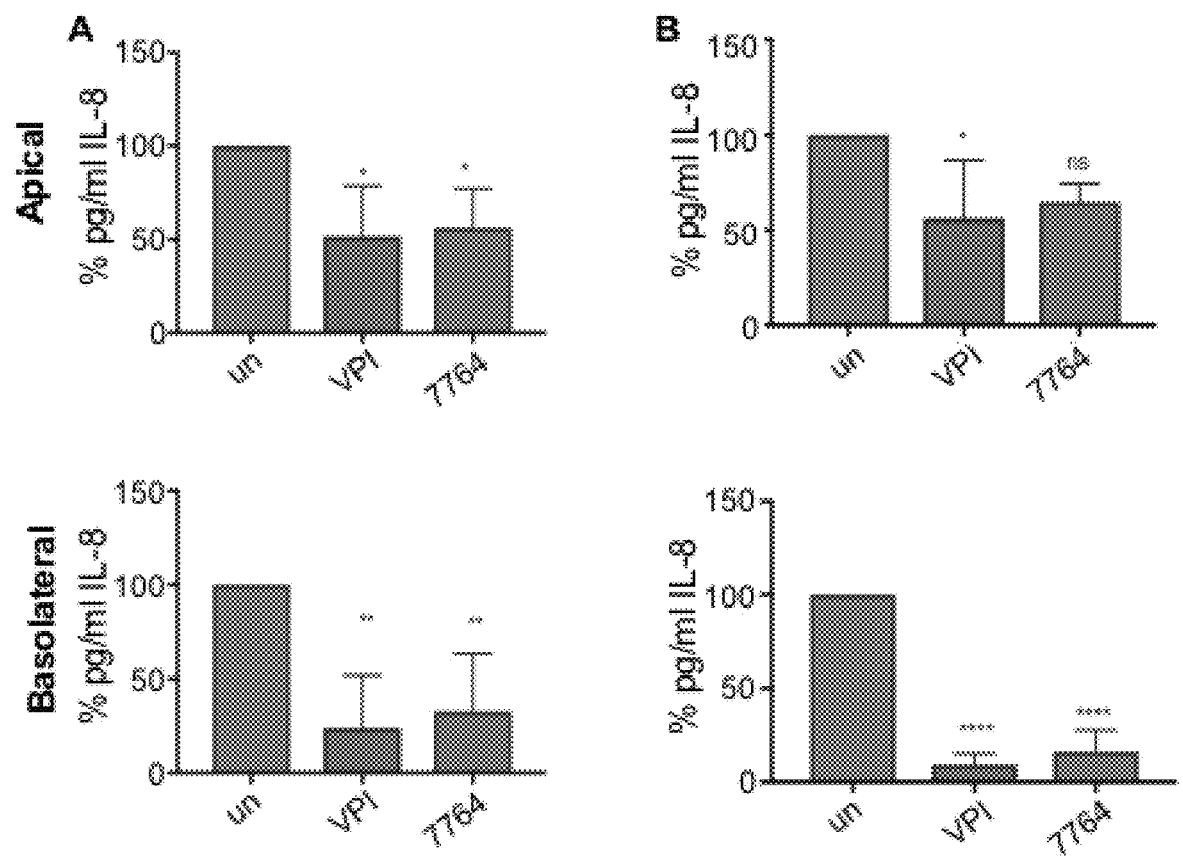
FIG. 17A shows IL-8 levels, determined by ELISA, produced by ΔCFTR Caco-2 lines grown on transwell filters for ~4 weeks. Addition of *B. theta* VPI 5482 (VPI) or the clinical isolate from a CF subject SMC7764 (7764) to the apical compartment of the transwell, is compared to the untreated control (un).
FIG. 17B shows IL-8 levels, determined by ELISA, produced by ΔCFTR Caco-2 lines after application of cell free supernatants supplemented with 100 ng/ml TNFα. For all panels, *p<0.05, p<0.01, *p<0.001 by the one-way ANOVA with a Dunnett's multiple comparisons post-test compared to the untreated (un) condition.

Apically inoculated *B. theta* significantly reduced both the apical and basolateral production of IL-8 of the ΔCFTR line (FIG. 17A), but not the WT line. A similar observation was made with a clinical *Bacteroides* isolate from a patient with CF (FIG. 17A, strain 7764). It is possible that the observed effects on the WT line are more modest because the starting IL-8 level in the WT line are lower than observed for the ΔCFTR line.

To investigate whether secreted products produced by these strains could also modulate IL-8 production, cell-free sterilized supernatant from the same strains tested in panel A were applied to the apical face of the Caco-2 cells and the filters were incubated anaerobically for three hours, the supernatant removed, and then fresh cell free supernatant supplemented with 100 ng/ml TNF☐ added and the filters were returned to anaerobic incubation overnight. The exchange of medium at 3 hrs was performed to mirror the washing step used with cells, as outlined in panel A. Twenty four hours after initial application of the bacterial supernatants, culture supernatants were collected and IL-8 levels measured via ELISA assay (PromoKine or Biolegend).

These supernatants effectively and significantly reduced basolateral IL-8 levels for both the ΔCFTR and WT lines (FIG. 17B) but had minimal effects on the apical expression of IL-8. Finally, given that culture supernatants could reduce IL-8 production, supernatants from an additional clinical strain isolated from an infant with CF were test and a significant reduction in IL-8 production for both the ΔCFTR and WT lines was observed, indicating that multiple isolates of *Bacteroides* spp. could reduce basolateral IL-8 production.

Example 2-5. Animal Studies

Germ free (GF) mice were utilized to test the relationship between a CF infant intestinal microbiota (as CF infant feces was inoculated into the GF mice) and markers of inflammation in the intestine, specifically calprotectin. In this study, 6 GF mice in one of two arms were inoculated with pooled feces from three infants with CF that show a paucity of *Bacteroides* spp. In parallel, 6 GF mice each were inoculated with feces from these same two infants that have both been supplemented with a pool of strains including the well-characterized lab strain, *Bacteroides thetaiotaomicron*

(commonly known at *B. theta*) and two clinical isolates. The total amount of *Bacteroides* supplemented into the treatment was ~8×10$^9$ CFU/5 ml of stool suspension. The control stool suspension had <10$^4$ CFU/5 ml of stool suspension. Mice were gavaged on days 1, 3, 6, and 15, and fecal samples collected on each day, as well as day 0 (before gavaging). Fecal samples were assessed for calprotectin levels, a marker of intestinal inflammation, by ELISA at day 0 and day 15.

Figure 18:
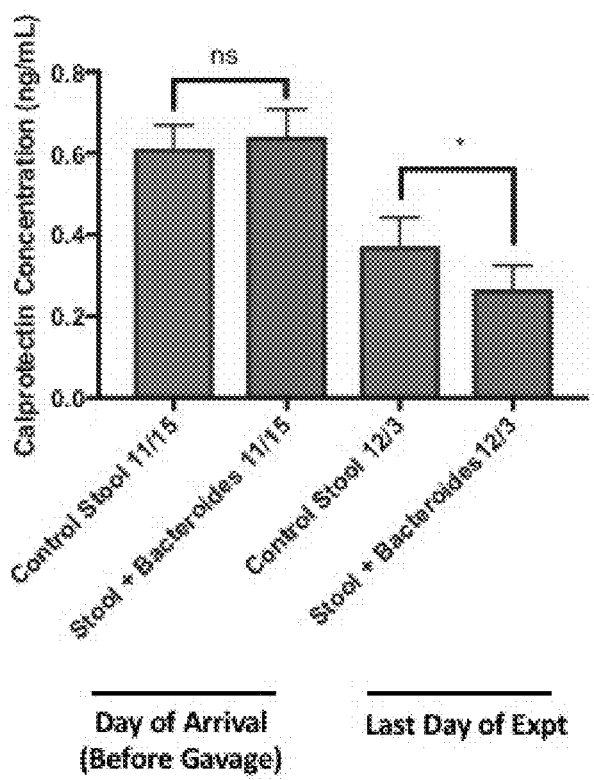
FIG. 18 shows calprotectin levels in mouse stool. The levels of stool calprotectin were measured at the day of arrival (Day 0, before gavage) and on the final day of the experiment. There was a significant reduction in in the level of calprotectin (ng/ml, as measured by ELISA) in stool collected on the last day of the experiment in the group treated with *Bacteroides*. *, P=0.0141 by paired T-test compared to control stool; ns=not significant.

The levels of stool calprotectin were measured at the day of arrival (Day 0, before gavage) and on the final day of the experiment. There was a significant reduction in in the level of calprotectin (ng/ml, as measured by ELISA) in stool collected on the last day of the experiment in the group treated with *Bacteroides*. *, P=0.0141 by paired T-test compared to control stool; ns=not significant (FIG. 18).

In this study, infants with CF have patterns in the intestinal microbiome that were distinct from healthy control infants as early as 6 weeks of life, and the composition of the communities remained distinct at 1 year of life. Interesting, only a small group of genera differed between the cohorts, including *Bacteroides* spp. While other studies have also shown a significant reduction in *Bacteroides* spp. in CF, these studies focused on older populations (>1 year old children, adolescents or adults), smaller cohorts, and/or reported a larger degree of dysbiosis with alterations (i.e., higher or lower relative abundance) in a number of different taxa, perhaps because older cohorts were targeted in these studies. Some reports also show changes in the abundance of *Escherichia coli* or other Enterobacteriaceae, although here consistent differences of these organisms in a larger cohort over the first year of life were not observed. Only *Bacteroides* spp. were consistently reduced over the first year of life in a cohort of 21 infants with CF who were less than 1 year old.

There was a significant reduction of *Bacteroides*, a critical immune-modulating microbe, and there does not appear to be a completely distinct microbiota in the CF cohort compared to the healthy controls in this age group. Importantly, there appears to be a link between gut microbial communities and airway disease, a finding further supported in this larger cohort. Thus, the inherent intestinal dysbiosis in CF beginning in early life may impact systemic inflammation and gut-derived immune response, which likely contributes to airway exacerbation. The in vitro data demonstrate that multiple isolates of *Bacteroides* spp., and their secreted products, applied to the apical face of an intestinal cell line, can reduce IL-8 secretion from both the apical and/or basolateral face of these intestinal cells, a finding consistent with another report in the literature that examined the impact of a *Bacteroides*-derived toxin. Supernatants of these clinical isolates seemed to be particularly efficient at reducing basolateral secretion of IL-8. Therefore, beneficial strains of *Bacteroides* can potentially alter systemic signals of inflammation, and thereby may potentially impact airway disease through this mechanism. Animal studies will further clarify this link between intestinal microflora and airway function.

Consistent with the in vitro data, the mouse studies shown in FIG. 7 and FIG. 8 showed a reduction in an intestinal marker of inflammation (calprotectin) compared to the control treatment with no added *Bacteroides*, indicating that the presence of *Bacteroides* does indeed appear to reduce inflammation in vivo.

There are several important implications of these findings. First, while enzyme replacement therapy has clearly had positive transformative impacts on patients with CF, the differences observed in the intestinal microbiota in individuals with CF indicate they still have underlying defects in intestinal microbiota and suggests a need for further therapeutic interventions. The fact that only a single species is significantly depleted over the first year of life (i.e., *Bacteroides* spp.) indicates that the alteration(s) in the CF intestinal environment mediated by loss of CFTR function might be relatively specific early in life. Additionally, this data, in combination with prior work, suggest that probiotic therapies or other interventions that shift the intestinal microbiota towards a more healthful state may mitigate pulmonary exacerbations. Several systematic reviews of randomized controlled trials of probiotics in groups with CF have shown a positive impact of probiotics on reducing frequency of CF exacerbation and improving gastrointestinal inflammation, however mechanisms underlying the observed benefits of shifting the intestinal microbiome in CF are not yet clear and these trials did not supplements the subjects with additional *Bacteroides*. Given that pulmonary exacerbations are associated with the progressive loss of lung function in this population, resulting in morbidity and ultimately premature mortality, using findings from this and similar studies to reduce the frequency of such clinical episodes beginning in early life would likely assist in maintaining lung function in patients with CF.

EQUIVALENTS

The foregoing written specification is considered to be sufficient to enable one skilled in the art to practice the embodiments. The foregoing description and Examples detail certain embodiments and describes the best mode contemplated. It will be appreciated, however, that no matter how detailed the foregoing may appear in text, the embodiment may be practiced in many ways and should be construed in accordance with the appended claims and any equivalents thereof.

References discussed in the application, which are incorporated by reference in their entirety, for their intended purpose, which is clear based upon its context.

Boucher R C. 2004. New concepts of the pathogenesis of cystic fibrosis lung disease. European Respiratory Journal 23:146-58.

Lyczak J B, et al. 2002. Lung infections associated with cystic fibrosis. Clin Microbiol Rev 15:194-222.

Huang N N, et al. 1961. The flora of the respiratory tract of patients with cystic fibrosis of the pancreas. J Pediat 59:512-521.

Deretic V, et al. 1993. Conversion to mucoidy in *Pseudomonas aeruginosa*. Biotechnology (N Y) 11:1133-6.

Govan J R, et al. 1992. Microbiology of lung infection in cystic fibrosis. Br Med Bull 48:912-30.

Castellani C, et al. 2017. Cystic fibrosis: a clinical view. Cell Mol Life Sci 74:129-140.

Madan J C, et al. 2012. Serial analysis of the gut and respiratory microbiome in CF in infancy: the interaction between intestinal and respiratory tracts and the impact of nutritional exposures. mBio 3:e00251-12.

Hoen A G, et al. 2015. Associations between gut microbial colonization in early life and respiratory outcomes in Cystic Fibrosis. J Pediatr 167:138-47 e1-3.

Chong C Y L, et al. Factors affecting gastrointestinal microbiome development in neonates. Nutrients 10.

Toscano M, et al. 2017. Role of the human breast milk-associated microbiota on the newborns' immune system: A mini review. Front Microbiol 8:2100.

Milani C, et al. 2017. The first microbial colonizers of the human gut: composition, activities, and health implications of the infant gut microbiota. Microbiol Mol Biol Rev. 81:e00036-171.

Gilbert-Diamond D, et al. 2016. Relation between in utero arsenic exposure and birth outcomes in a cohort of mothers and their newborns from New Hampshire. Environ Health Perspect 124:1299-307.

Fei D L, et al. 2013. Association between in utero arsenic exposure, placental gene expression, and infant birth weight: a US birth cohort study. Environ Health 12:58.

Farzan S F, et al. 2013. In utero arsenic exposure and infant infection in a United States cohort: a prospective study. Environ Res 126:24-30.

Zhao J, et al. 2012. Decade-long bacterial community dynamics in cystic fibrosis airways. Proc Natl Acad Sci USA 109:5809-14.

Filkins L M, et al. 2012. Prevalence of streptococci and increased polymicrobial diversity associated with cystic fibrosis patient stability. J Bacteriol 194:4709-17.

Price K E, et al. 2013. Unique microbial communities persist in individual cystic fibrosis patients throughout a clinical exacerbation. Microbiome 1:27.

Carmody L A, et al. 2013. Changes in cystic fibrosis airway microbiota at pulmonary exacerbation. Ann Am Thorac Soc 10:179-87.

Fodor A A, et al. 2012. The adult cystic fibrosis airway microbiota is stable over time and infection type, and highly resilient to antibiotic treatment of exacerbations. PLoS One 7:e45001.

Hisert K B, et al. 2017. Restoring Cystic Fibrosis Transmembrane Conductance Regulator function reduces airway bacteria and inflammation in people with cystic fibrosis and chronic lung infections. Am J Respir Crit Care Med 195:1617-1628.

Wolter D J, et al. 2013. *Staphylococcus aureus* small-colony variants are independently associated with worse lung disease in children with cystic fibrosis. Clin Infect Dis 57:384-91.

Maier E, et al. 2014. Understanding how commensal obligate anaerobic bacteria regulate immune functions in the large intestine. Nutrients 7:45-73.

Thaiss C A, et al. 2014. The interplay between the innate immune system and the microbiota. Curr Opin Immunol 26:41-8.

Billard L, et al. 2017. Viruses in cystic fibrosis patients' airways. Crit Rev Microbiol 43:690-708.

Smyth A. 2016. Treatment of pulmonary exacerbations in cystic fibrosis—could do better? Paediatr Respir Rev 20 Suppl:6-7.

Pittman J E, et al. 2014. Cystic fibrosis: NHLBI Workshop on the Primary Prevention of Chronic Lung Diseases. Ann Am Thorac Soc 11 Suppl 3:S161-8.

Kim J M, et al. 2001. Polarized secretion of CXC chemokines by human intestinal epithelial cells in response to *Bacteroides fragilis* enterotoxin: NF-kappa B plays a major role in the regulation of IL-8 expression. Clin Exp Immunol 123:421-7.

Ozen Alandab Y, et al. 2016. Pancreatic involvement in cystic fibrosis. Minerva Med 107:427-436.

Schindler T, et al. 2015. Nutrition management of cystic fibrosis in the 21st century. Nutr Clin Pract 30:488-500.

Flight W G, et al. 2015. Rapid detection of emerging pathogens and loss of microbial diversity associated with severe lung disease in cystic fibrosis. J Clin Microbiol 53:2022-9.

Cosseau C, et al. 2008. The commensal *Streptococcus salivarius* K12 downregulates the innate immune responses of human epithelial cells and promotes host-microbe homeostasis. Infect Immun 76:4163-75.

Gifford A H, et al. 2014. Iron supplementation does not worsen respiratory health or alter the sputum microbiome in cystic fibrosis. J Cyst Fibros 13:311-8.

Hampton T H, et al. 2014. The microbiome in pediatric cystic fibrosis patients: the role of shared environment suggests a window of intervention. Microbiome 2:14.

Langille M G, et al. 2013. Predictive functional profiling of microbial communities using 16S rRNA marker gene sequences. Nat Biotechnol 31:814-21.

Gensollen T, et al. 2016. How colonization by microbiota in early life shapes the immune system. Science 352:539.

Vangay P., et al. 2015. Antibiotics, pediatric dysbiosis, and disease. Cell Host and Microbe 17 (5), 553-564.

Chen J, et al. 2012. Associating microbiome composition with environmental covariates using generalized UniFrac distances. Bioinformatics 28: 2106-2113.

Mougeot J-L C, et al. 2016. Concordance of HOMIM and HOMINGS technologies in the microbiome analysis of clinical samples. J Oral Microbiol. 8: 30379

Belstrøm D, et al. 2016. Salivary bacterial fingerprints of established oral disease revealed by the Human Oral Microbe Identification using Next Generation Sequencing (HOMINGS) technique. J Oral Microbiol. 8:30170.

Gomes B P, et al. 2015. Microbiomes of endodontic-periodontal lesions before and after chemomechanical preparation. J Endod. 41(12):1975-84.

Madan J C, et al. 2016. Association of Cesarean Delivery and Formula Supplementation With the Intestinal Microbiome of 6-Week-Old Infants. JAMA Pediatr. 170(3):212-9.

Madan J C (2016) Neonatal gastrointestinal and respiratory microbiome in cystic fibrosis: potential interactions and implications for systemic health. Clinical therapeutics 38(4):740-746.

Scanlan P D, et al. (2012) Gut dysbiosis in cystic fibrosis. J Cyst Fibros 11(5):454-455.

Rogers G B, et al. (2016) The CF gastrointestinal microbiome: Structure and clinical impact. Pediatric pulmonology 51(S44):S35-s44.

Farrelly P J, et al. (2014) Gastrointestinal surgery in cystic fibrosis: a 20-year review. J Pediatr Surg 49(2):280-283.

Bodewes F A, et al. (2015) Cystic fibrosis and the role of gastrointestinal outcome measures in the new era of therapeutic CFTR modulation. J Cyst Fibros 14(2):169-177.

Boczar M, et al. (2015) Meconium ileus in newborns with cystic fibrosis—results of treatment in the group of patients operated on in the years 2000-2014. Developmental period medicine 19(1):32-40.

Dorsey J, et al. (2017) Bacterial overgrowth, dysbiosis, inflammation, and dysmotility in the Cystic Fibrosis intestine. Journal of cystic fibrosis: official journal of the European Cystic Fibrosis Society 16 Suppl 2:S14-s23.

Woestenenk J W, et al. (2015) Pancreatic enzyme replacement therapy and coefficient of fat absorption in children and adolescents with cystic fibrosis. J Pediatr Gastroenterol Nutr 61(3):355-360.

Madan J C, et al. ((2016) Association of Cesarean delivery and formula supplementation with the intestinal microbiome of 6 week old infants. JAMA Pediatrics.

Lyons A, et al. Bacterial strain-specific induction of Foxp3+ T regulatory cells is protective in murine allergy models. Clin Exp Allergy (2010) 40(5):811-9.

Isolauri E, et al. Probiotics: effects on immunity. Am J Clin Nutr (2001) 73(2 Suppl):444S-50S Butel M-J, et al. Conditions of bifidobacterial colonization in preterm infants: a prospective analysis. J Pediatr Gastroenterol Nutr (2007) 44(5):577-82.

Fanning S. et al. Bifidobacterial surface-exopolysaccharide facilitates commensal-host interaction through immune modulation and pathogen protection. Proc Natl Acad Sci USA (2012) 109(6):2108-13.

Abdulkadir B. et al. Routine use of probiotics in preterm infants: longitudinal impact on the microbiome and metabolome. Neonatology (2016) 109(4):239-47.

Kim J M, et al. (2001) Polarized secretion of CXC chemokines by human intestinal epithelial cells in response to *Bacteroides fragilis* enterotoxin: NF-kappa B plays a major role in the regulation of IL-8 expression. Clinical and experimental immunology 123(3):421-427.

de Freitas M B, et al. Altered intestinal microbiota composition, antibiotic therapy and intestinal inflammation in children and adolescents with cystic fibrosis. PLoS One. 2018; 13(6):e0198457.

Miragoli F, et al. Impact of cystic fibrosis disease on archaea and bacteria composition of gut microbiota. FEMS Microbiol Ecol. 2016; 93(2):fiw230.

Flass T, Tong S, Frank D N, et al. Intestinal lesions are associated with altered intestinal microbiome and are more frequent in children and young adults with cystic fibrosis and cirrhosis. PLoS One. 2015; 10(2):e0116967.

Bruzzese E, et al. Disrupted intestinal microbiota and intestinal inflammation in children with cystic fibrosis and its restoration with *Lactobacillus* GG: a randomised clinical trial. PLoS One. 2014; 9(2):e87796.

Matamouros S, et al. Adaptation of commensal proliferating *Escherichia coli* to the intestinal tract of young children with cystic fibrosis. Proc Natl Acad Sci USA. 2018; 115(7):1605-1610.

Hoffman L R, et al. *Escherichia coli* dysbiosis correlates with gastrointestinal dysfunction in children with cystic fibrosis. Clin Infect Dis. 2013; 58(3):396-9.

Anderson J L, et al. (2017) Effect of probiotics on respiratory, gastrointestinal and nutritional outcomes in patients with cystic fibrosis: A systematic review. Journal of cystic fibrosis: official journal of the European Cystic Fibrosis Society 16(2):186-197.

Van Biervliet S, et al. (2017) Clinical effects of probiotics in cystic fibrosis patients: A systematic review. Clinical nutrition ESPEN 18:37-43.

Ananthan A, et al. (2016) Probiotic supplementation in children with cystic fibrosis-a systematic review. European journal of pediatrics 175(10):1255-1266.

R Core Team (2018). R: A language and environment for statistical computing. R Foundation for Statistical Computing, Vienna, Austria. URL https://www.R-project.org/.

Callahan B J. et al. (2016). "DADA2: High-resolution sample inference from Illumina amplicon data." Nature Methods, *13*, 581-583.

Yilmaz P. et al. (2014) The SILVA and "All-species Living Tree Project (LTP)" taxonomic frameworks. Nucleic Acids Research, 42(1):643-648.

McMurdie, P, et al. (2013). "phyloseq: An R package for reproducible interactive analysis and graphics of microbiome census data". PLoS ONE 8(4):e61217.

Schliep K. P. (2011). "phangorn: phylogenetic analysis in R". Bioinformatics, 27(4) 592-593

Dixon, P. (2003), "VEGAN, a package of R functions for community ecology". Journal of Vegetation Science, 14: 927-930.

Hao, S., et al. "Inactivation of CFTR by CRISPR/Cas9 alters transcriptional regulation of inflammatory pathways and other networks". Journal of Cystic Fibrosis, in review.

What is claimed is:

1. A method of altering the intestinal microbiome in a patient diagnosed with cystic fibrosis, wherein the patient is 0 days to 6 months old and has a relative abundance of intestinal *Bacteroides* of not more than 20%, a relative abundance of intestinal *Bifidobacterium* of not more than 20%, or both, the method comprising:
   administering at least one of *Bifidobacterium* or *Bacteroides* to the patient's gastrointestinal tract and allowing the *Bifidobacterium* or *Bacteroides* to alter the intestinal microbiome, wherein altering the intestinal microbiome reduces the risk of, reduces the severity of, or delays the onset of a pulmonary infection or pulmonary exacerbation.

2. The method of claim 1, wherein the method comprises administering both *Bifidobacterium* and *Bacteroides*.

3. The method of claim 1, wherein the pulmonary infection is selected from the group consisting of *Staphylococcus aureus* infection, *Pseudomonas aeruginosa* infection, *Stenotrophomonas* infection, *Streptococcus* infection, *Haemophilus influenzae* infection, nontuberculous *mycobacterium* infection, *Burkholderia cepacia* complex infection, viral infection, fungal infection, and a co-infection with multiple pathogens.

4. A method of preventing, delaying the onset, reducing the severity, and/or reducing the duration of a pulmonary infection by a pathogen, or an exacerbation thereof, in a patient in need thereof, the method comprising:
   administering to the patient at least one of *Bifidobacterium* or *Bacteroides* to the patient's gastrointestinal tract, wherein prior to said administration a fecal sample from the patient has been tested to determine a level of *Bifidobacterium* or *Bacteroides* in the patient's gastrointestinal tract;
   wherein the patient is 0 days old to 6 months old.

5. The method of claim 4, wherein the pathogen is *P. aeruginosa*.

6. The method of claim 4, wherein the patient is 1 week old to 6 months old.

7. The method of claim 4, wherein the patient is a cystic fibrosis patient.

8. A method of treating cystic fibrosis in a patient in need thereof, the method comprising:
   administering an effective amount of cystic fibrosis therapy to the patient thereby treating cystic fibrosis, wherein the cystic fibrosis therapy is selected from the group consisting of:
   (i) at least one pancreatic enzyme replacement product;
   (ii) at least one probiotic;
   (iii) at least one prebiotic;
   (iv) at least one antibiotic;
   (v) at least one anti-inflammatory medication;
   (vi) at least one mucus-thinning drug;
   (vii) at least one cystic fibrosis transmembrane conductance regulator (CFTR) function-improving medication;
   (viii) at least one bronchodilator or inhaled medication; and
   (ix) a combination thereof;
   wherein, prior to said administration, a fecal sample from the patient has been tested to determine whether the patient has a decreased level of *Bifidobacterium* or *Bacteroides* relative to a healthy control population and the patient has a relative abundance of intestinal *Bacteroides* of not more than 20%, a relative abundance of intestinal *Bifidobacterium* of not more than 20%, or both.

9. The method of claim 8, wherein the method comprises reducing the risk of, severity of, or delaying at least one cystic fibrosis-associated outcome.

10. The method of claim 9, wherein the cystic-fibrosis associated outcome is pulmonary exacerbation.

11. The method of claim 8, wherein the patient is a pediatric patient.

12. The method of claim 8, wherein the method comprises reducing systemic levels of interleukin-8.

13. The method of claim 1, wherein the relative abundance of intestinal *Bifidobacterium* in the patient at age 4 months is not more than 20%.

14. The method of claim 1, wherein the *Bifidobacterium* or *Bacteroides* is orally administered to the patient.

15. The method of claim 4, wherein the fecal sample has a relative abundance of *Bacteroides* of not more than 20%.

16. The method of claim 4, wherein the fecal sample has a relative abundance of *Bacteroides* of ≤1%.

17. The method of claim 16, wherein the patient is not a cystic fibrosis patient.

18. The method of claim 4, wherein the patient is about 4 months old and the fecal sample has a relative abundance of *Bifidobacterium* of not more than 20%.

19. The method of claim 4, wherein the *Bifidobacterium* or *Bacteroides* is orally administered to the patient.

20. A method of preventing, delaying the onset, reducing the severity, and/or reducing the duration of a pulmonary infection by a pathogen in a patient that is age 6 months or less, the method comprising:
    obtaining a fecal sample from the patient;
    testing the fecal sample to determine a level of *Bifidobacterium* or *Bacteroides*, wherein a relative abundance of *Bifidobacterium* of not more than 20%, a relative abundance of *Bacteroides* of not more than 20%, or both indicates that the patient is at risk for a pulmonary infection;
    administering *Bifidobacterium* or *Bacteroides* to the patient's gastrointestinal tract.

21. The method of claim 20, wherein the patient is not a cystic fibrosis patient.

22. The method of claim 21, wherein the *Bifidobacterium* or *Bacteroides* is orally administered to the patient.

23. The method of claim 20, wherein the patient is a cystic fibrosis patient.

24. The method of claim 23, wherein the *Bifidobacterium* or *Bacteroides* is orally administered to the patient.

25. The method of claim 1, wherein the patient is age 4 months or less.

26. The method of claim 20, wherein the patient is age 4 months or less.

27. A method of reducing the risk of, reducing the severity of, or delaying a pulmonary exacerbation in a patient in need thereof, the method comprising:
    administering to the patient at least one of *Bifidobacterium* or *Bacteroides* to the patient's gastrointestinal tract, wherein prior to said administration a fecal sample from the patient has been tested to determine a level of *Bifidobacterium* or *Bacteroides* in the patient's gastrointestinal tract;
    wherein the patient is 0 days old to 6 months old.

28. The method of claim 27, wherein the pulmonary exacerbation is associated with a pathogenic microbial infection.

29. The method of claim 28, wherein the pathogenic microbial infection is selected from the group consisting of *Staphylococcus aureus* infection, *Pseudomonas aeruginosa* infection, *Stenotrophomonas* infection, *Streptococcus* infection, *Haemophilus influenzae* infection, nontuberculous mycobacterium infection, *Burkholderia cepacia* complex infection, viral infection, fungal infection, and a co-infection with multiple pathogens.

30. The method of claim 27, wherein the patient is a cystic fibrosis patient.

31. The method of claim 27, wherein the *Bifidobacterium* or *Bacteroides* is orally administered to the patient.

\* \* \* \* \*